US009855046B2

(12) United States Patent
Shalev

(10) Patent No.: US 9,855,046 B2
(45) Date of Patent: Jan. 2, 2018

(54) VASCULAR BANDS AND DELIVERY SYSTEMS THEREFOR

(75) Inventor: Alon Shalev, Ra'anana (IL)

(73) Assignee: ENDOSPAN LTD., Herzilyia Pituach (IL)

(*) Notice: Subject to any disclaimer, the term of this patent is extended or adjusted under 35 U.S.C. 154(b) by 1154 days.

(21) Appl. No.: 13/979,551

(22) PCT Filed: Feb. 16, 2012

(86) PCT No.: PCT/IL2012/000083
§ 371 (c)(1),
(2), (4) Date: Jul. 12, 2013

(87) PCT Pub. No.: WO2012/111006
PCT Pub. Date: Aug. 23, 2012

(65) Prior Publication Data
US 2013/0289587 A1 Oct. 31, 2013

Related U.S. Application Data

(60) Provisional application No. 61/443,740, filed on Feb. 17, 2011.

(51) Int. Cl.
A61F 2/06 (2013.01)
A61B 17/12 (2006.01)
(Continued)

(52) U.S. Cl.
CPC .......... A61B 17/12022 (2013.01); A61F 2/07 (2013.01); A61B 17/12 (2013.01); A61F 2/89 (2013.01); A61F 2002/065 (2013.01)

(58) Field of Classification Search
CPC ..... A61B 17/12022; A61B 17/12; A61F 2/07; A61F 2/89; A61F 2002/065
See application file for complete search history.

(56) References Cited

U.S. PATENT DOCUMENTS 4,355,426 A 10/1982 MacGregor
4,505,767 A 3/1985 Quin
(Continued)

FOREIGN PATENT DOCUMENTS

CA 2 497 704 3/2004
EP 1 177 780 2/2002
(Continued)

OTHER PUBLICATIONS

Communication dated Nov. 10, 2014 from the European Patent Office in counterpart application No. 12752054.2.
(Continued)

Primary Examiner — Sarah W Aleman
Assistant Examiner — Rachel S Highland
(74) Attorney, Agent, or Firm — Sughrue Mion, PLLC

(57) ABSTRACT

An extra-luminal ring (1200) includes a structural member (1202), which assumes a first elongate hollow shape (1206) when in a relaxed state; when deformed to a planar state (1208), generally defines a planar shape (1209) having two first sides (1220A, 1220B) parallel to each other, and two second sides (1222A, 1222B) parallel to each other; and when in the relaxed state, is configured such that the two first sides (1220A, 1220B) are generally straight and parallel with each other, and the two second sides (1222A, 1222B) are curved at least partially around a first longitudinal axis (1230) defined by the first elongate hollow shape (1206). The structural member (1202), when in a deformed state, has a second elongate hollow shape (1240), different from the first elongate hollow shape (1206), in which the two second sides (1222A, 1222B) are generally straight and parallel with each other, and the two first sides (1220A, 1220B) are curved at least partially around a second longitudinal axis (1250) defined by the second elongate hollow shape (1240).

26 Claims, 17 Drawing Sheets

(51) Int. Cl.
*A61F 2/89* (2013.01)
*A61F 2/07* (2013.01)

(56) References Cited

U.S. PATENT DOCUMENTS

| | | | |
|---|---|---|---|
| 4,562,596 A | 1/1986 | Kornberg | |
| 4,577,631 A | 3/1986 | Kreamer | |
| 4,617,932 A | 10/1986 | Kornberg | |
| 4,665,906 A | 5/1987 | Jervis | |
| 4,739,762 A | 4/1988 | Palmaz | |
| 4,787,899 A | 11/1988 | Lazarus | |
| 4,878,906 A | 11/1989 | Lindemann et al. | |
| 4,886,062 A | 12/1989 | Wiktor | |
| 4,938,740 A | 7/1990 | Melbin | |
| 4,969,458 A | 11/1990 | Wiktor | |
| 5,042,707 A | 8/1991 | Taheri | |
| 5,064,435 A | 11/1991 | Porter | |
| 5,104,404 A | 4/1992 | Wolff | |
| 5,122,136 A | 6/1992 | Guglielmi et al. | |
| 5,133,732 A | 7/1992 | Wiktor | |
| 5,234,448 A | 8/1993 | Wholey | |
| 5,486,183 A | 1/1996 | Middleman et al. | |
| 5,507,769 A | 4/1996 | Marin et al. | |
| 5,509,923 A | 4/1996 | Middleman et al. | |
| 5,522,880 A | 6/1996 | Barone et al. | |
| 5,527,322 A | 6/1996 | Klein et al. | |
| 5,549,662 A | 8/1996 | Fordenbacher | |
| 5,554,181 A | 9/1996 | Das | |
| 5,556,413 A | 9/1996 | Lam | |
| 5,562,724 A | 10/1996 | Vorwerk et al. | |
| 5,607,445 A | 3/1997 | Summers | |
| 5,613,974 A | 3/1997 | Andreas et al. | |
| 5,632,746 A | 5/1997 | Middleman et al. | |
| 5,632,763 A | 5/1997 | Glastra | |
| 5,632,772 A | 5/1997 | Alcime et al. | |
| 5,639,278 A | 6/1997 | Dereume et al. | |
| 5,643,340 A | 7/1997 | Nunokawa | |
| 5,653,743 A | 8/1997 | Martin | |
| 5,676,696 A | 10/1997 | Marcade | |
| 5,676,697 A | 10/1997 | McDonald | |
| 5,728,134 A | 3/1998 | Barak | |
| 5,749,879 A | 5/1998 | Middleman et al. | |
| 5,755,770 A | 5/1998 | Ravenscroft | |
| 5,755,771 A | 5/1998 | Penn et al. | |
| 5,755,777 A | 5/1998 | Chuter | |
| 5,755,781 A | 5/1998 | Jayaraman | |
| 5,769,882 A | 6/1998 | Fogarty et al. | |
| 5,769,884 A | 6/1998 | Solovay | |
| 5,782,903 A | 7/1998 | Wiktor | |
| 5,782,906 A | 7/1998 | Marshall et al. | |
| 5,824,040 A | 10/1998 | Cox et al. | |
| 5,827,321 A | 10/1998 | Roubin | |
| 5,843,170 A | 12/1998 | Ahn | |
| 5,855,600 A | 1/1999 | Alt | |
| 5,860,991 A | 1/1999 | Klein et al. | |
| 5,876,432 A | 3/1999 | Lau et al. | |
| 5,906,641 A | 5/1999 | Thompson et al. | |
| 5,921,994 A | 7/1999 | Andreas et al. | |
| 5,980,552 A | 11/1999 | Pinchasik | |
| 6,015,431 A | 1/2000 | Thornton et al. | |
| 6,016,810 A | 1/2000 | Ravenscroft | |
| 6,033,435 A | 3/2000 | Penn et al. | |
| 6,036,725 A | 3/2000 | Avellanet | |
| 6,049,824 A | 4/2000 | Taheri | |
| 6,099,497 A | 8/2000 | Adams et al. | |
| 6,117,145 A | 9/2000 | Wood et al. | |
| 6,156,064 A | 12/2000 | Chouinard | |
| 6,200,339 B1 | 3/2001 | Leschinsky et al. | |
| 6,206,893 B1 | 3/2001 | Klein et al. | |
| 6,270,524 B1 | 8/2001 | Kim | |
| 6,283,991 B1 | 9/2001 | Cox et al. | |
| 6,290,720 B1 | 9/2001 | Khosravi et al. | |
| 6,296,661 B1 | 10/2001 | Davila et al. | |
| 6,312,458 B1 | 11/2001 | Golds | |
| 6,325,823 B1 | 12/2001 | Horzewski et al. | |
| 6,344,056 B1 | 2/2002 | Dehdashtian | |
| 6,406,420 B1 | 6/2002 | McCarthy | |
| 6,428,565 B1 | 8/2002 | Wisselink | |
| 6,506,211 B1 | 1/2003 | Skubitz et al. | |
| 6,613,078 B1 | 9/2003 | Barone | |
| 6,635,083 B1 | 10/2003 | Cheng et al. | |
| 6,648,911 B1 | 11/2003 | Sirhan | |
| 6,652,567 B1 | 11/2003 | Deaton | |
| 6,656,214 B1 | 12/2003 | Fogarty et al. | |
| 6,692,520 B1 | 2/2004 | Gambale et al. | |
| 6,695,833 B1 | 2/2004 | Frantzen | |
| 6,743,195 B2 | 6/2004 | Zucker | |
| 6,752,826 B2 | 6/2004 | Holloway | |
| 6,776,794 B1 | 8/2004 | Hong et al. | |
| 6,808,534 B1 * | 10/2004 | Escano | A61F 2/07 |
| | | | 604/96.01 |
| 6,814,749 B2 | 11/2004 | Cox et al. | |
| 6,814,752 B1 | 11/2004 | Chuter | |
| 6,824,560 B2 | 11/2004 | Pelton | |
| 6,846,321 B2 | 1/2005 | Zucker | |
| 6,907,285 B2 | 6/2005 | Denker et al. | |
| 6,908,477 B2 | 6/2005 | McGuckin, Jr. et al. | |
| 6,929,660 B1 | 8/2005 | Ainsworth et al. | |
| 6,942,691 B1 | 9/2005 | Chuter | |
| 6,964,679 B1 | 11/2005 | Marcade et al. | |
| 6,986,774 B2 | 1/2006 | Middleman et al. | |
| 7,008,441 B2 | 3/2006 | Zucker | |
| 7,044,962 B2 | 5/2006 | Elliott | |
| 7,105,020 B2 | 9/2006 | Greenberg et al. | |
| 7,112,217 B1 | 9/2006 | Kugler et al. | |
| 7,115,127 B2 | 10/2006 | Lindenbaum et al. | |
| 7,144,421 B2 | 12/2006 | Carpenter et al. | |
| 7,201,772 B2 | 4/2007 | Schwammenthal et al. | |
| 7,223,266 B2 | 5/2007 | Lindenbaum et al. | |
| 7,270,675 B2 | 9/2007 | Chun et al. | |
| 7,279,003 B2 | 10/2007 | Berra et al. | |
| 7,294,147 B2 | 11/2007 | Hartley | |
| 7,306,623 B2 | 12/2007 | Watson | |
| 7,341,598 B2 | 3/2008 | Davidson et al. | |
| 7,407,509 B2 | 8/2008 | Greenberg et al. | |
| 7,429,269 B2 | 9/2008 | Schwammenthal et al. | |
| 7,442,204 B2 | 10/2008 | Schwammenthal et al. | |
| 7,473,272 B2 | 1/2009 | Pryor | |
| 7,537,609 B2 | 5/2009 | Davidson et al. | |
| 7,540,881 B2 | 6/2009 | Meyer et al. | |
| 7,544,160 B2 | 6/2009 | Gross | |
| 7,637,939 B2 | 12/2009 | Tischler | |
| 7,662,161 B2 | 2/2010 | Briganti et al. | |
| 7,662,168 B2 | 2/2010 | McGuckin, Jr. et al. | |
| 7,678,141 B2 | 3/2010 | Greenan et al. | |
| 7,708,704 B2 | 5/2010 | Mitelberg | |
| 7,722,626 B2 | 5/2010 | Middleman et al. | |
| 7,731,732 B2 | 6/2010 | Ken | |
| 7,803,178 B2 | 9/2010 | Whirley et al. | |
| 7,815,673 B2 | 10/2010 | Bloom et al. | |
| 7,887,575 B2 | 2/2011 | Kujawski | |
| 7,959,662 B2 | 6/2011 | Erbel et al. | |
| 8,021,418 B2 | 9/2011 | Gerberding et al. | |
| 8,066,755 B2 | 11/2011 | Zacharias et al. | |
| 8,080,053 B2 | 12/2011 | Satasiya et al. | |
| 8,157,810 B2 | 4/2012 | Case et al. | |
| 8,172,892 B2 | 5/2012 | Chuter et al. | |
| 8,251,963 B2 | 8/2012 | Chin et al. | |
| 8,353,898 B2 | 1/2013 | Lutze et al. | |
| 8,486,131 B2 | 7/2013 | Shalev | |
| 2001/0004705 A1 | 6/2001 | Killion | |
| 2001/0014823 A1 | 8/2001 | Ressemann et al. | |
| 2001/0044651 A1 | 11/2001 | Steinke et al. | |
| 2001/0044652 A1 | 11/2001 | Moore | |
| 2001/0047198 A1 | 11/2001 | Drasler et al. | |
| 2001/0053930 A1 | 12/2001 | Kugler et al. | |
| 2002/0040236 A1 * | 4/2002 | Lau | A61F 2/07 |
| | | | 623/1.12 |
| 2002/0099438 A1 * | 7/2002 | Furst | A61F 2/91 |
| | | | 623/1.16 |
| 2002/0099441 A1 | 7/2002 | Dehdashtian | |
| 2002/0107564 A1 | 8/2002 | Cox | |
| 2002/0123791 A1 | 9/2002 | Harrison | |
| 2002/0156495 A1 | 10/2002 | Brenneman et al. | |

(56) References Cited

U.S. PATENT DOCUMENTS

| | | |
|---|---|---|
| 2003/0040791 A1 | 2/2003 | Oktay |
| 2003/0068296 A1 | 4/2003 | Ricci et al. |
| 2003/0093145 A1 | 5/2003 | Lawrence-Brown et al. |
| 2003/0125796 A1 | 7/2003 | Dong |
| 2003/0130720 A1 | 7/2003 | DePalma et al. |
| 2003/0144725 A1* | 7/2003 | Lombardi ............. A61F 2/07 623/1.13 |
| 2003/0153968 A1 | 8/2003 | Geis et al. |
| 2003/0191523 A1 | 10/2003 | Hojeibane |
| 2003/0199967 A1 | 10/2003 | Hartley et al. |
| 2003/0199968 A1* | 10/2003 | Ainsworth ............. A61F 2/915 623/1.16 |
| 2003/0204236 A1 | 10/2003 | Letort |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0133266 A1 | 7/2004 | Clerc et al. |
| 2004/0171978 A1 | 9/2004 | Shalaby |
| 2004/0181149 A1 | 9/2004 | Langlotz et al. |
| 2004/0215319 A1 | 10/2004 | Berra et al. |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0149166 A1 | 7/2005 | Schaeffer et al. |
| 2005/0154448 A1 | 7/2005 | Cully et al. |
| 2005/0171598 A1 | 8/2005 | Schaeffer et al. |
| 2005/0177132 A1 | 8/2005 | Lentz et al. |
| 2005/0203606 A1 | 9/2005 | VanCamp |
| 2005/0216018 A1 | 9/2005 | Sennett et al. |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0234542 A1 | 10/2005 | Melsheimer |
| 2005/0266042 A1 | 12/2005 | Tseng |
| 2005/0283188 A1* | 12/2005 | Loshakove ........ A61B 17/0057 606/213 |
| 2006/0015170 A1 | 1/2006 | Jones et al. |
| 2006/0052799 A1 | 3/2006 | Middleman et al. |
| 2006/0069426 A1 | 3/2006 | Weinberger |
| 2006/0100684 A1 | 5/2006 | Elliott |
| 2006/0106406 A1 | 5/2006 | Weinberger |
| 2006/0149360 A1 | 7/2006 | Schwammenthal et al. |
| 2006/0155358 A1 | 7/2006 | LaDuca et al. |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0281966 A1 | 12/2006 | Peacock, III |
| 2007/0021822 A1 | 1/2007 | Boatman |
| 2007/0043425 A1 | 2/2007 | Hartley et al. |
| 2007/0050011 A1 | 3/2007 | Klein |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0167898 A1 | 7/2007 | Peters et al. |
| 2007/0179598 A1 | 8/2007 | Duerig |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0109066 A1 | 5/2008 | Quinn |
| 2008/0114445 A1 | 5/2008 | Melsheimer et al. |
| 2008/0147173 A1 | 6/2008 | McIff et al. |
| 2008/0167704 A1 | 7/2008 | Wright et al. |
| 2008/0195190 A1* | 8/2008 | Bland ............... A61F 2/91 623/1.11 |
| 2008/0195191 A1 | 8/2008 | Luo |
| 2008/0215134 A1 | 9/2008 | Lawrence-Brown |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030502 A1 | 1/2009 | Sun et al. |
| 2009/0048663 A1 | 2/2009 | Greenberg |
| 2009/0054967 A1 | 2/2009 | Das |
| 2009/0069881 A1 | 3/2009 | Chalekian et al. |
| 2009/0069882 A1 | 3/2009 | Venturelli |
| 2009/0082841 A1 | 3/2009 | Zacharias et al. |
| 2009/0099648 A1 | 4/2009 | Yu |
| 2009/0099649 A1 | 4/2009 | Chobotov et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev |
| 2010/0070019 A1 | 3/2010 | Shalev |
| 2010/0161026 A1 | 6/2010 | Brocker et al. |
| 2010/0211159 A1 | 8/2010 | Schmid et al. |
| 2010/0256725 A1 | 10/2010 | Rasmussen |
| 2010/0292774 A1* | 11/2010 | Shalev ............... A61F 2/06 623/1.13 |
| 2011/0093002 A1 | 4/2011 | Rucker et al. |
| 2011/0125251 A1 | 5/2011 | Cottone |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0264184 A1 | 10/2011 | Heltai |
| 2012/0179236 A1 | 7/2012 | Benary |
| 2012/0323305 A1 | 12/2012 | Benary |

FOREIGN PATENT DOCUMENTS

| | | |
|---|---|---|
| EP | 1 325 716 | 7/2003 |
| JP | 2002-253682 | 9/2002 |
| WO | 98/06355 A1 | 2/1998 |
| WO | 99/34748 A1 | 7/1999 |
| WO | 03/099108 | 12/2003 |

(56) References Cited

FOREIGN PATENT DOCUMENTS

| | | |
|---|---|---|
| WO | 2004/017868 | 3/2004 |
| WO | 05/002466 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 06/070372 | 7/2006 |
| WO | 2007/084547 | 7/2007 |
| WO | 2007/144782 | 12/2007 |
| WO | 08/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 08/107885 | 9/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 09/118733 | 10/2009 |
| WO | 10/031060 | 3/2010 |
| WO | 2010/024869 | 3/2010 |
| WO | 2010/024879 | 3/2010 |
| WO | 2010/027704 A1 | 3/2010 |
| WO | 2010/045238 | 4/2010 |
| WO | 2010/062355 | 6/2010 |
| WO | 10/088776 | 8/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |
| WO | 2012/049679 | 4/2012 |
| WO | 2012/104842 | 8/2012 |
| WO | 2012/111006 | 8/2012 |
| WO | 2012/117395 | 9/2012 |
| WO | 2012/176187 | 12/2012 |
| WO | 2013/005207 | 1/2013 |
| WO | 2013/030818 | 3/2013 |
| WO | 2013/030819 | 3/2013 |
| WO | 2013/065040 | 5/2013 |
| WO | 2013/084235 | 6/2013 |
| WO | 2013/171730 | 11/2013 |

OTHER PUBLICATIONS

Communication dated Aug. 15, 2014 from the United States Patent and Trademark Office in counterpart U.S. Appl. No. 13/939,798.
Communication dated Sep. 2, 2014 from the United States Patent and Trademark Office in counterpart U.S. Appl. No. 12/447,684.
Communication dated Nov. 28, 2014 from the European Patent Office in counterpart application No. 08861980.4.
An English translation of Office Action dated Nov. 28, 2013 which issued during the prosecution of Chinese Patent Application No. 200880126889.0.
An Office Action dated Apr. 28, 2014, which issued during the prosecution of U.S. Appl. No. 13/939,798.
"E-vita® open plus" product brochure (JOTEC GmbH, Hechingen, Germany), 2010.
Fonseca A et al., "Intravascular ultrasound assessment of the novel AngioSculpt scoring balloon catheter for the treatment of complex coronary lesions," J Invasive Cardiol 20(1):21-7 (Jan. 2008).
Khlif H et al., "Contribution to the Improvement of Textile Vascular Prostheses Crimping," Trends in Applied Sciences Research 6(9):1019-1027 (2011).
An International Search Report dated Sep. 29, 2008, which issued during the prosecution of Applicant's PCT/IL08/000287.
A Written Opinion dated Sep. 29, 2008, which issued during the prosecution of Applicant's PCT/IL08/000287.
An International Search Report dated Feb. 4, 2011, which issued during the prosecution of Applicant's PCT/IB2010/052861.
A Written Opinion dated Feb. 4, 2011, which issued during the prosecution of Applicant's PCT/IB2010/052861.
An International Search Report dated Dec. 3, 2010, which issued during the prosecution of Applicant's PCT/IL2010/000564.
A Written Opinion dated Dec. 3, 2010, which issued during the prosecution of Applicant's PCT/IL2010/000564.
An International Search Report dated Nov. 5, 2010, which issued during the prosecution of Applicant's PCT/IL2010/000549.
A Written Opinion dated Nov. 5, 2010, which issued during the prosecution of Applicant's PCT/IL2010/000549.
An International Search Report dated Aug. 4, 2011, which issued during the prosecution of Applicant's PCT/IL2010/000999.
An International Search Report dated Mar. 10, 2011, which issued during the prosecution of Applicant's PCT/IL2010/000917.
An International Search Report dated Mar. 30, 2011, which issued during the prosecution of Applicant's PCT/IL2010/001018.
An International Search Report dated Apr. 18, 2011, which issued during the prosecution of Applicant's PCT/IL2010/001037.
An International Search Report dated May 23, 2011, which issued during the prosecution of Applicant's PCT/IL2010/001087.
An International Search Report dated Jun. 28, 2011, which issued during the prosecution of Applicant's PCT/IL2011/000135.
An International Search Report dated Jun. 30, 2009, which issued during the prosecution of Applicant's PCT/IL2008/001621.
A Written Opinion dated Jun. 30, 2009, which issued during the prosecution of Applicant's PCT/IL2008/001621.
An International Search Report dated Mar. 11, 2009, which issued during the prosecution of Applicant's PCT/IL2007/001312.
A Written Opinion dated Mar. 11, 2009, which issued during the prosecution of Applicant's PCT/IL2007/001312.
An Office Action dated Aug. 25, 2011, which issued Chinese Patent Application No. 200880014919.9.
An Office Action dated Nov. 12, 2010, which issued during the prosecution of U.S. Appl. No. 12/447,684.
An Office Action dated Apr. 27, 2011, which issued during the prosecution of U.S. Appl. No. 12/447,684.
An International Preliminary Report on Patentability dated Aug. 4, 2009, which of Applicant's PCT/IL2007/001312.
An English Abstract of JP2002-253682 published Sep. 10, 2002.
An International Search Report and a Written Opinion both dated Jul. 13, 2012, which issued during the prosecution of Applicant's PCT/IL2012/000083.
An International Search Report and a Written Opinion both dated Mar. 15, 2013, which issued during the prosecution of Applicant's PCT/IL2012/050424.
U.S. Appl. No. 61/448,199, filed Mar. 2, 2011.
U.S. Appl. No. 61/014,031, filed Dec. 15, 2007.
An Examiner Interview Summary Report dated Dec. 13, 2010, which issued during the prosecution of U.S. Appl. No. 12/447,684.
U.S. Appl. No. 60/863,373, filed Oct. 29, 2006.
An Office Action together with its English Translation dated Feb. 16, 2013 which issued during the prosecution of Chinese Patent Application No. 200880126998.0.
A Restriction Requirement dated Mar. 21, 2012, which issued during the prosecution of U.S. Appl. No. 12/808,037.
An Office Action dated Jun. 19, 2012, which issued during the prosecution of U.S. Appl. No. 12/808,037.
An Office Action dated Feb. 27, 2013, which issued during the prosecution of U.S. Appl. No. 12/808,037.
A Notice of Allowance dated May 22, 2013, which issued during the prosecution of U.S. Appl. No. 12/808,037.
An International Search Report and a Written Opinion both dated Jul. 17, 2012, which issued during the prosecution of Applicant's PCT/IL2012/000095.

(56) References Cited

OTHER PUBLICATIONS

An International Preliminary Report on Patentability dated Sep. 3, 2013, which issued during the prosecution of Applicant's PCT/IL2012/000095.
An International Search Report on Patentability dated Aug. 21, 2013, which issued during the prosecution of Applicant's PCT/IL2012/000083.
An International Search Report and a Written Opinion both dated Oct. 4, 2012, which issued during the prosecution of Applicant's PCT/IL2012/000269.
An International Search Report and a Written Opinion both dated Aug. 31, 2012, which issued during the prosecution of Applicant's PCT/IL2012/000148.
An International Search Report and a Written Opinion both dated Sep. 6, 2012, which issued during the prosecution of Applicant's PCT/IL2012/000190.
An International Search Report and a Written Opinion both dated Sep. 24, 2012, which issued during the prosecution of Applicant's PCT/IL2012/00060.
An International Search Report and a Written Opinion both dated Oct. 1, 2012, which issued during the prosecution of Applicant's PCT/IL2012/000241.
An Office Action dated Oct. 11, 2012, which issued during the prosecution of U.S. Appl. No. 13/031,871.
U.S. Appl. No. 61/443,740, filed Feb. 17, 2011.
An Office Action dated Feb. 25, 2013, which issued during the prosecution of U.S. Appl. No. 13/031,871.
An Extended European Search Report dated Dec. 13, 2012, which issued Applicant's European App No. 08719912.1.

* cited by examiner

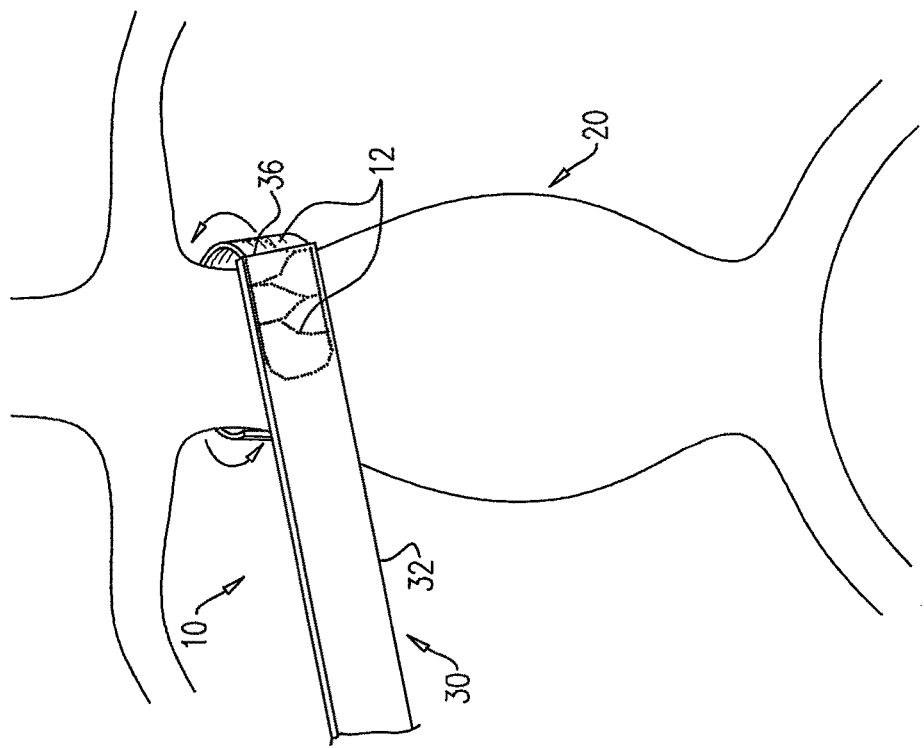
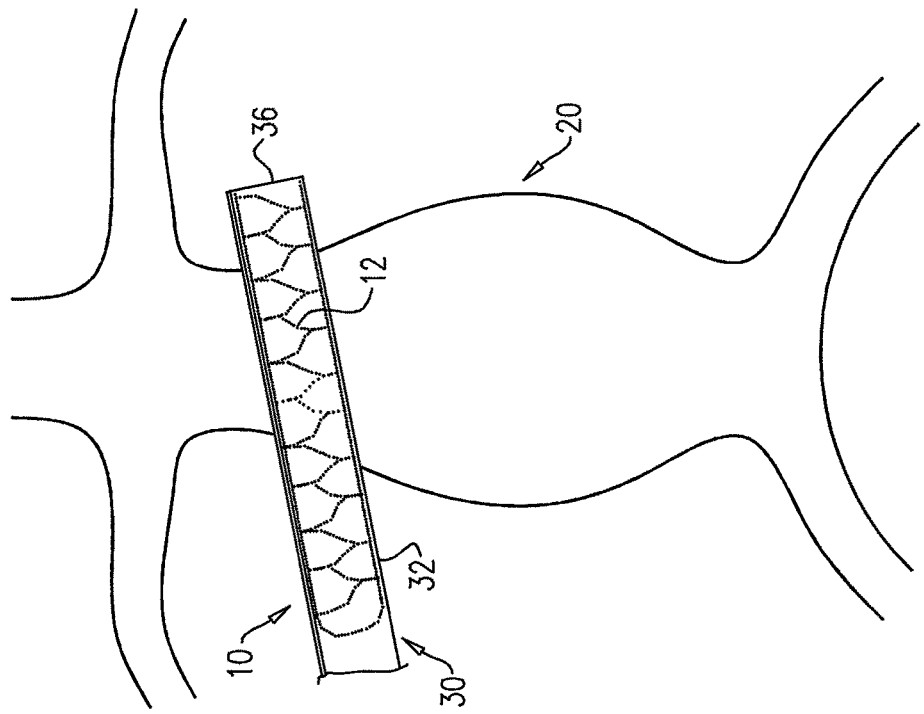

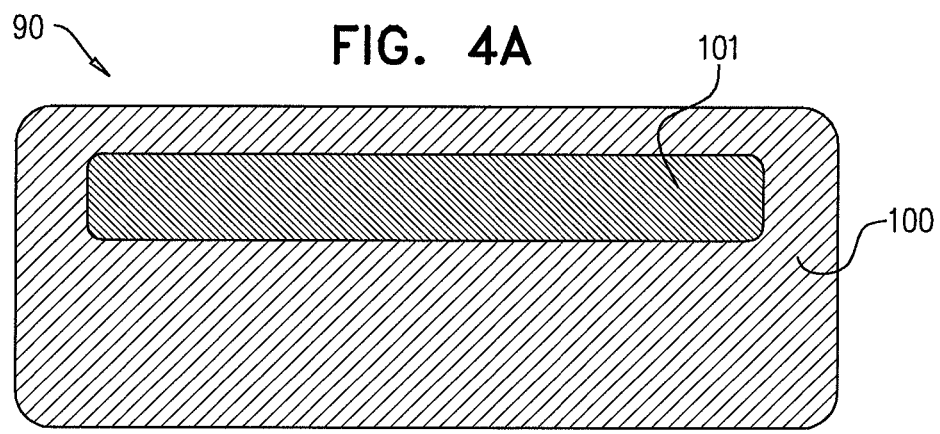
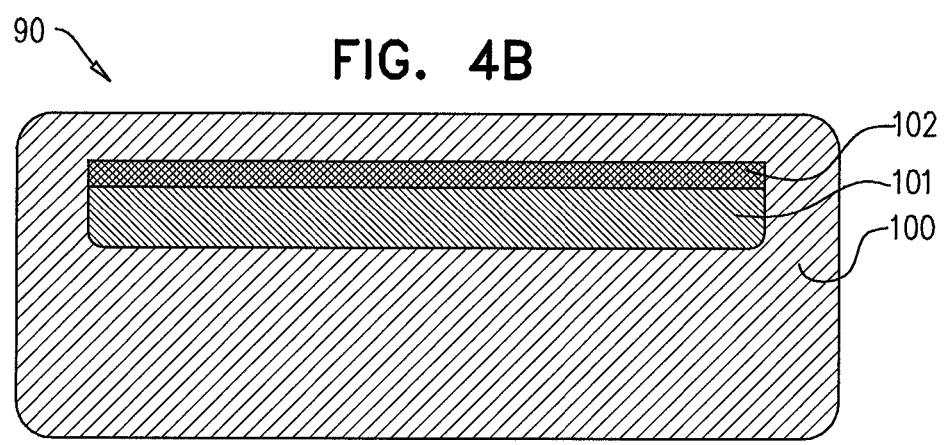

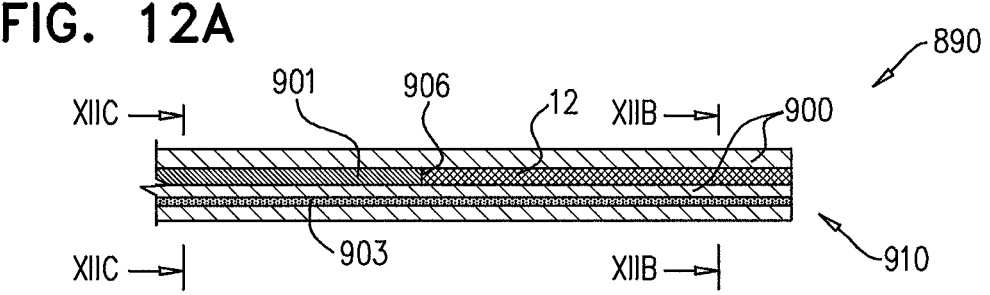
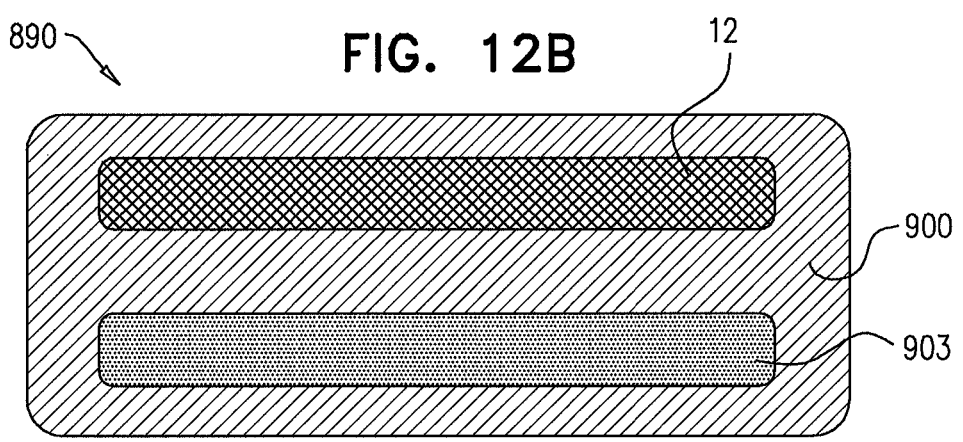
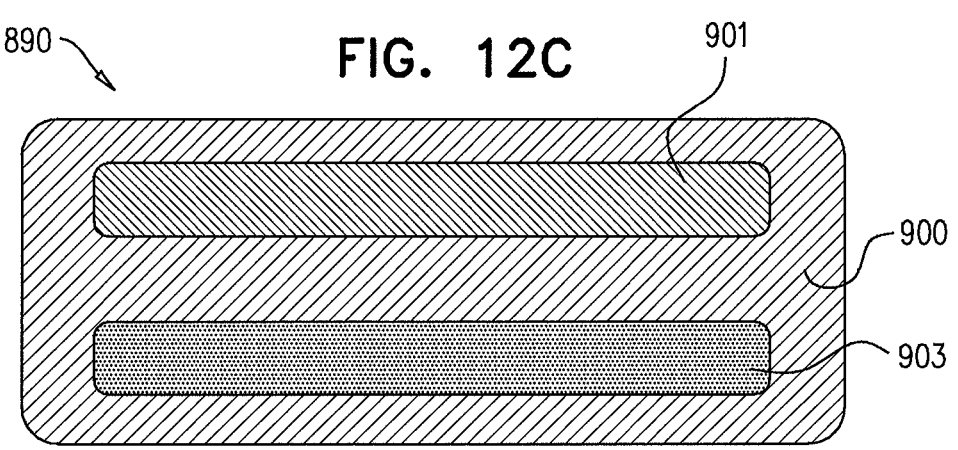

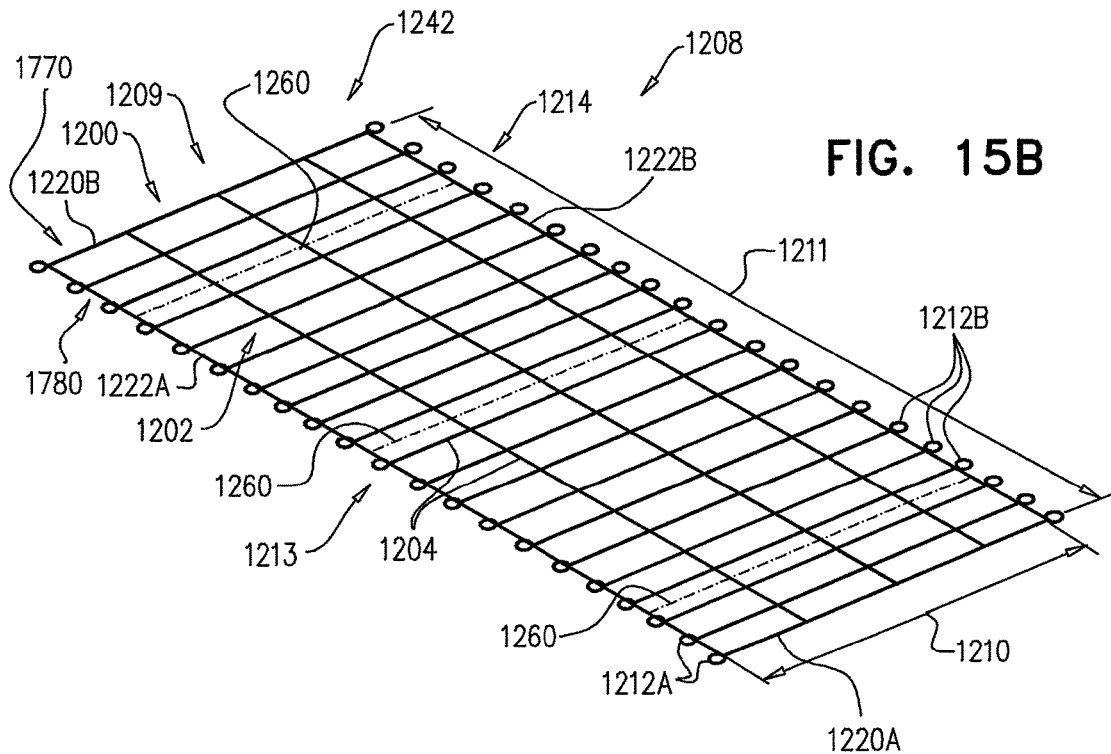
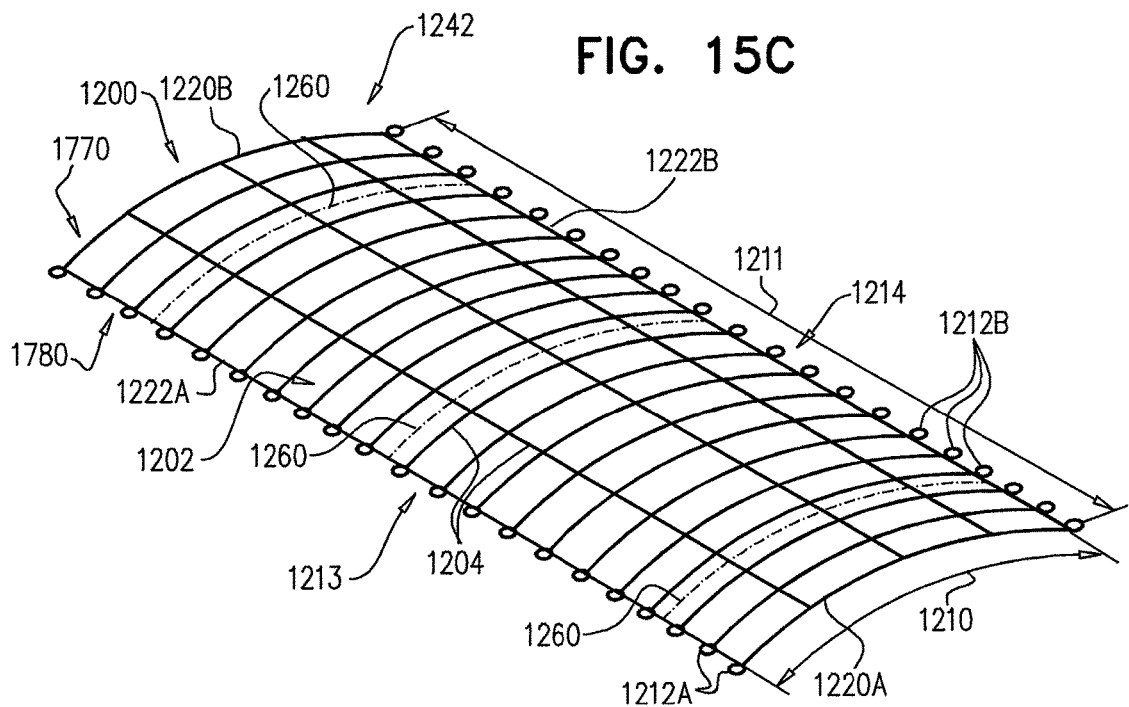

VASCULAR BANDS AND DELIVERY SYSTEMS THEREFOR

CROSS-REFERENCE TO RELATED APPLICATIONS

The present patent application is the National Stage of International Application PCT/IL2012/000083, filed Feb. 16, 2012, which claims priority from U.S. Provisional Application 61/443,740, filed Feb. 17, 2011, which is assigned to the assignee of the present application and is incorporated herein by reference.

FIELD OF THE APPLICATION

The present invention relates generally to implantable medical devices, and specifically to delivery tools and implantable vascular bands.

BACKGROUND OF THE APPLICATION

An aneurysm is a localized, blood-filled dilation (bulge) of a blood vessel caused by disease or weakening of the vessel wall. Left untreated, the aneurysm will frequently rupture, resulting in loss of blood through the rupture and death. Aneurysms are commonly classified by shape, structure and location. Aortic aneurysms are the most common form of arterial aneurysm and are life-threatening. It is common for an aortic aneurysm to occur in the portion of the abdominal aorta between the renal arteries and the iliac arteries. Aneurysms in the abdominal aorta are associated with particularly high mortality; accordingly, current medical standards call for urgent operative repair when aneurysm diameter is larger than 5 cm. Abdominal surgery, however, results in substantial stress to the body. Although the mortality rate for an aortic aneurysm is extremely high, there is also considerable mortality and morbidity associated with open surgical intervention to repair an aortic aneurysm.

Therefore, less invasive techniques have been developed to treat an aortic aneurysm without the attendant risks of intra-abdominal surgery. These techniques include transvascularly introducing an endovascular stent-graft into the aorta. The neck of the aorta at the cephalad end (i.e., above the aneurysm) is usually sufficient to maintain attachment of a stent-graft to the wall of the aorta. However, when an aneurysm is located near the iliac arteries, there may be an ill-defined neck or no neck below the aneurysm. Such an ill-defined neck may provide insufficient healthy aortic tissue to which to successfully mount a stent-graft. Furthermore, much of the abdominal aorta wall may be calcified which may make it difficult to attach the stent-graft to the aortic wall. Unfavorable anatomy relating to the neck of the aneurysm is the most common reason for patients being rejected for Endovascular Repair of Abdominal Aortic Aneurysm (EVAR). A short or absent infrarenal neck, large aortic diameters, and excessive angulation at this level are the main problems. Furthermore, progressive expansion of the aneurysm sac associated with type I endoleak can lead to compromise of the seal at the neck and is the principal indication for secondary intervention for this condition.

PCT Publication WO 2009/078010 to Shalev, and US Patent Application Publication 2010/0292774 in the national stage thereof, which are assigned to the assignee of the present application and is incorporated herein by reference, describe a system for treating an aneurysmatic abdominal aorta, comprising (a) an extra-vascular wrapping (EVW) comprising (i) at least one medical textile member adapted to at least partially encircle a segment of aorta in proximity to the renal arteries, and (ii) a structural member, wherein the EVW is adapted for laparoscopic delivery, and (b) an endovascular stent-graft (ESG) comprising (i) a compressible structural member, and (ii) a substantially fluid impervious fluid flow guide (FFG) attached thereto. Also described is an extra-vascular ring (EVR) adapted to encircle the neck of an aortic aneurysm. Further described are methods for treating an abdominal aortic aneurysm, comprising laparoscopically delivering the extra-vascular wrapping (EVW) and endovascularly placing an endovascular stent-graft (ESG). Also described are methods to treat a type I endoleak. U.S. Provisional Application 61/014,031, filed Dec. 15, 2007, from which the above-referenced applications claim priority, is also incorporated herein by reference.

SUMMARY OF THE APPLICATION

In some applications of the present invention, an extra-luminal ring is configured to assume first and second different elongate hollow shapes, which are curled in different directions from each other. The extra-luminal ring comprises a structural member, which typically comprises a shape memory material. When in a relaxed state, the structural member is configured to assume the first elongate hollow shape, and is suitable for being placed around a tubular organ, e.g., an aorta. When laparoscopically deployed around the neck of an aneurysmal aorta, such as a sub-renal neck, a supra-renal neck, an ascending aortic neck, or a neck adjacent the right subclavian artery, the extra-luminal ring creates a landing zone for an endovascular stent-graft implanted during an Endovascular Repair of Abdominal Aortic Aneurysm (EVAR) procedure.

The structural member, if deformed to a planar state, generally defines a planar shape having two first sides parallel to each other, and two second sides parallel to each other. When in the relaxed state described above, the structural member is configured such that (i) the two first sides are generally straight and parallel with each other, and (ii) the two second sides are curved at least partially around a first longitudinal axis defined by the first elongate hollow shape.

For delivery during an implantation procedure, the structural member is placed in a deformed state, in which the structural member has the second elongate hollow shape mentioned above. When in this deformed state, (i) the two second sides are generally straight and parallel with each other, and (ii) the two first sides are curved at least partially around a second longitudinal axis defined by the second elongate hollow shape. Typically, the structural member is restrained in the deformed state while placed in a delivery shaft for transluminal delivery to the target tubular organ, e.g., the aorta.

For some applications, the structural member is shaped so as to define a first plurality of engagement members disposed along a first one of the two second sides, and a second plurality of engagement members disposed along a second one of the two second sides. The first plurality of engagement members: (i) engage the second plurality of engagement members when the structural member is in the deformed state, and (ii) do not engage the second plurality of engagement members when the structural member is in the relaxed state.

For some applications, the first elongate hollow shape geometrically defines a plurality of line segments that are straight and parallel to the first longitudinal axis, when the structural member is in the relaxed state. When the structural member is in the deformed state, the plurality of line segments geometrically defined by first elongate hollow shape are curved at least partially around the second longitudinal axis.

For some applications, when the extra-luminal ring is in the deformed state, a longitudinal engagement element, such as a wire, when positioned passing through first and the second pluralities of engagement members, removably engages the first plurality of engagement members with the second plurality of engagement members. Removal of the longitudinal engagement element from the first and second pluralities of engagement members allows the structural member to transition to the relaxed state when otherwise no longer deformed. For some applications, the structural member is configured to automatically transition from the deformed state to the relaxed state as the structural member is deployed from the delivery shaft, and the longitudinal engagement element, if provided, is slidingly proximally withdrawn from the engagement members.

The structural member, if deformed to the planar state, defines first and second surfaces facing away from each other. For some applications, (i) when the structural member has the first elongate hollow shape in the relaxed state, the first surface faces radially inward and the second surface faces radially outward, and (ii) when the structural member has the second elongate hollow shape in the deformed state, the first surface faces radially outward and the second surface faces radially inward. Thus, for these applications, deploying the extra-luminal ring from the delivery shaft everts the structural member. For some of these applications, the structural member is configured to evert itself during a transition from the deformed state to the relaxed state, during deployment from the delivery shaft. Typically, the shape memory of the structural member causes this eversion.

There is therefore provided, in accordance with an application of the present invention, apparatus including:

an extra-luminal ring, which includes a structural member, which (a) is configured to assume a first elongate hollow shape when in a relaxed state, (b) when deformed to a planar state, generally defines a planar shape having two first sides parallel to each other, and two second sides parallel to each other, and (c) when in the relaxed state, is configured such that (i) the two first sides are generally straight and parallel with each other, and (ii) the two second sides are curved at least partially around a first longitudinal axis defined by the first elongate hollow shape; and a hollow, generally tubular delivery shaft, in which the extra-luminal ring is removably disposed with the structural member in a deformed state, in which state (a) the structural member has a second elongate hollow shape, different from the first elongate hollow shape, (b) the two second sides are generally straight and parallel with each other, and (c) the two first sides are curved at least partially around a second longitudinal axis defined by the second elongate hollow shape.

For some applications, the planar shape is a parallelogram, and the structural member generally defines the parallelogram when deformed to the planar state. For some applications, the parallelogram is a rectangle, and the structural member generally defines the rectangle when deformed to the planar state. For some applications, a ratio of (a) a length of each of the second sides to (b) a length of each of the first sides is at least 6:1.

For some applications, the first elongate hollow shape is generally cylindrical, and the structural member is configured to assume the generally cylindrical first elongate hollow shape when in the relaxed state. Alternatively or additionally, for some applications, the second elongate hollow shape is generally cylindrical, and wherein, when the extra-luminal ring is removably disposed in the delivery shaft in the deformed state, the structural member has the generally cylindrical second elongate hollow shape.

Optionally, the planar shape has rounded corners.

For some applications, the structural member, when in the relaxed state, is configured such that the two first sides are generally parallel with the first longitudinal axis. Alternatively or additionally, for some applications, the structural member, when in the deformed state, is configured such that the two second sides are generally parallel with the second longitudinal axis.

Typically, the structural member is configured to automatically transition from the deformed state to the relaxed state as the structural member is deployed from the delivery shaft.

For any of the applications described above, the structural member, when deformed to the planar state, may define first and second surfaces facing away from each other; when the structural member has the first elongate hollow shape in the relaxed state, the first surface may face radially inward and the second surface may face radially outward; and when the structural member has the second elongate hollow shape in the deformed state, the first surface may face radially outward and the second surface may face radially inward.

For any of the applications described above, the structural member may be configured to evert itself during a transition from the deformed state to the relaxed state, during deployment from the delivery shaft.

For any of the applications described above, the structural member may be shaped so as to define a first plurality of engagement members disposed along a first one of the two second sides, and a second plurality of engagement members disposed along a second one of the two second sides, and the first plurality of engagement members (a) may engage the second plurality of engagement members when the extra-luminal ring is removably disposed in the delivery shaft with the structural member in the deformed state, and (b) may not engage the second plurality of engagement members when the structural member is in the relaxed state. The first plurality of engagement members may optionally extend outside of the planar shape generally defined by the structural member when deformed to the planar state. Alternatively or additionally, the second plurality of engagement members may optionally extend outside of the planar shape generally defined by the structural member when deformed to the planar state. For some applications, the apparatus further includes a longitudinal engagement element, which, when positioned passing through the first and the second pluralities of engagement members, engages the first plurality of engagement members with the second plurality of engagement members. For some applications, the longitudinal engagement element includes a wire or a hollow tube.

For any of the applications described above, the structural member may include a plurality of stent struts. For some applications, when the structural member is deformed to the planar state, the stent struts are arranged such that a first portion of the stent struts are parallel to the two first sides, and a second portion of the stent struts are parallel to the two second sides.

For any of the applications described above, the structural member may include a shape memory material.

For any of the applications described above, the first elongate hollow shape assumed by the structural member when in the relaxed state may be that of an elongate hollow structure that subtends an arc of less than 360 degrees.

For any of the applications described above, each of the first sides may have a length of between 1 and 4 cm, and each of the second sides may have a length of between 6 and 15 cm.

For any of the applications described above, the extra-luminal ring may be suitable for being placed at least partially around an aorta when the structural member is in the relaxed state.

For any of the applications described above, a portion of the delivery shaft in which the extra-luminal ring is removably disposed may have an inner diameter of between 8 and 15 mm.

There is further provided, in accordance with an application of the present invention, apparatus including:

an extra-luminal ring, which includes a structural member, which is configured, when in a relaxed state, to assume a first elongate hollow shape, which geometrically defines a plurality of line segments that are straight and parallel to a first longitudinal axis defined by the first elongate hollow shape; and a hollow, generally tubular delivery shaft, in which the extra-luminal ring is removably disposed with the structural member in a deformed state, in which state (a) the structural member has a second elongate hollow shape, different from the first elongate hollow shape, and (b) the plurality of line segments geometrically defined by the first elongate hollow shape are curved at least partially around a second longitudinal axis defined by the second elongate hollow shape.

For some applications, the first elongate hollow shape is generally cylindrical, and the structural member is configured to assume the generally cylindrical first elongate hollow shape when in the relaxed state. Alternatively or additionally, for some applications, the second elongate hollow shape is generally cylindrical, and wherein, when the extra-luminal ring is removably disposed in the delivery shaft in the deformed state, the structural member has the generally cylindrical second elongate hollow shape.

Typically, the structural member is configured to automatically transition from the deformed state to the relaxed state as the structural member is deployed from the delivery shaft.

For any of the applications described above, the structural member, when deformed to a planar state, may define first and second surfaces facing away from each other; when the structural member has the first elongate hollow shape in the relaxed state, the first surface may face radially inward and the second surface may face radially outward; and when the structural member has the second elongate hollow shape in the deformed state, the first surface may face radially outward and the second surface may face radially inward.

For any of the applications described above, the structural member may be configured to evert itself during a transition from the deformed state to the relaxed state, during deployment from the delivery shaft.

For any of the applications described above, the structural member may include a plurality of stent struts.

For any of the applications described above, the structural member may include a shape memory material.

For any of the applications described above, the first elongate hollow shape assumed by the structural member when in the relaxed state may be that of an elongate hollow structure that subtends an arc of less than 360 degrees.

For any of the applications described above, the extra-luminal ring may be suitable for being placed at least partially around an aorta when the structural member is in the relaxed state.

For any of the applications described above, a portion of the delivery shaft in which the extra-luminal ring is removably disposed may have an inner diameter of between 8 and 15 mm.

There is still further provided, in accordance with an application of the present invention, a method including:

providing an extra-luminal ring, which includes a structural member, which (a) is configured to assume a first elongate hollow shape when in a relaxed state, (b) when deformed to a planar state, generally defines a planar shape having two first sides parallel to each other, and two second sides parallel to each other, and (c) when in the relaxed state, is configured such that (i) the two first sides are generally straight and parallel with each other, and (ii) the two second sides are curved at least partially around a first longitudinal axis defined by the first elongate hollow shape; and advancing, to an external surface of a target blood vessel, a hollow, generally tubular delivery shaft, in which the extra-luminal ring is removably disposed with the structural member in a deformed state, in which state (a) the structural member has a second elongate hollow shape, different from the first elongate hollow shape, (b) the two second sides are generally straight and parallel with each other, and (c) the two first sides are curved at least partially around a second longitudinal axis defined by the second elongate hollow shape.

For some applications, the method further includes, after advancing the delivery shaft, deploying the extra-luminal ring from the delivery shaft such that the structural member transitions from the deformed state to the relaxed state and at least partially surrounds the blood vessel.

For some applications, the blood vessel is an aorta, and deploying includes deploying the extra-luminal ring at least partially around the aorta. For some applications, deploying includes deploying the extra-luminal ring from the delivery shaft such that the structural member automatically transitions from the deformed state to the relaxed state. For some applications, deploying includes deploying the extra-luminal ring from the delivery shaft such the structural member everts itself during a transition from the deformed state to the relaxed state during deployment from the delivery shaft. For some applications, deploying includes deploying the extra-luminal ring from the delivery shaft such that structural member assumes the first elongate hollow shape which subtends an arc of less than 360 degrees around the blood vessel. Alternatively, for some applications, deploying includes deploying the extra-luminal ring from the delivery shaft such that structural member assumes the first elongate hollow shape which completely surrounds the blood vessel.

For some applications, the planar shape is a parallelogram, and providing the extra-luminal ring includes providing the extra-luminal ring including the structural member that generally defines the parallelogram when deformed to the planar state. For some applications, the parallelogram is a rectangle, and providing the extra-luminal ring includes providing the extra-luminal ring including the structural member that generally defines the rectangle when deformed to the planar state.

For some applications, the first elongate hollow shape is generally cylindrical, and providing the extra-luminal ring includes providing the extra-luminal ring including the structural member configured to assume the generally cylindrical first elongate hollow shape when in the relaxed state.

Alternatively or additionally, for some applications, the second elongate hollow shape is generally cylindrical, and advancing includes advancing the delivery shaft when the extra-luminal ring is removably disposed in the delivery shaft in the deformed state, such that the structural member has the generally cylindrical second elongate hollow shape.

For some applications, the structural member, when deformed to the planar state, defines first and second surfaces facing away from each other; when the structural member has the first elongate hollow shape in the relaxed state, the first surface faces radially inward and the second surface faces radially outward; and when the structural member has the second elongate hollow shape in the deformed state, the first surface faces radially outward and the second surface faces radially inward.

For some applications, providing the extra-luminal ring includes providing the extra-luminal ring including the structural member that is shaped so as to define a first plurality of engagement members disposed along a first one of the two second sides, and a second plurality of engagement members disposed along a second one of the two second sides, and the first plurality of engagement members (a) engage the second plurality of engagement members when the extra-luminal ring is removably disposed in the delivery shaft with the structural member in the deformed state, and (b) do not engage the second plurality of engagement members when the structural member is in the relaxed state. For some applications, the method further includes providing a longitudinal engagement element, which, when positioned passing through the first and the second pluralities of engagement members, engages the first plurality of engagement members with the second plurality of engagement members.

For some applications, providing the extra-luminal ring includes providing the extra-luminal ring having the structural member that includes a shape memory material.

There is additionally provided, in accordance with an application of the present invention, a method including:

providing an extra-luminal ring, which includes a structural member, which is configured, when in a relaxed state, to assume a first elongate hollow shape, which geometrically defines a plurality of line segments that are straight and parallel to a first longitudinal axis defined by the first elongate hollow shape; and advancing, to an external surface of a target blood vessel, a hollow, generally tubular delivery shaft, in which the extra-luminal ring is removably disposed with the structural member in a deformed state, in which state (a) the structural member has a second elongate hollow shape, different from the first elongate hollow shape, and (b) the plurality of line segments geometrically defined by the first elongate hollow shape are curved at least partially around a second longitudinal axis defined by the second elongate hollow shape.

For some applications, the method further includes, after advancing the delivery shaft, deploying the extra-luminal ring from the delivery shaft such that the structural member transitions from the deformed state to the relaxed state and at least partially surrounds the blood vessel. For some applications, the blood vessel is an aorta, and deploying includes deploying the extra-luminal ring at least partially around the aorta. For some applications, deploying includes deploying the extra-luminal ring from the delivery shaft such that the structural member automatically transitions from the deformed state to the relaxed state.

The present invention will be more fully understood from the following detailed description of embodiments thereof, taken together with the drawings, in which:

BRIEF DESCRIPTION OF THE DRAWINGS

FIGS. 1A-D are schematic illustrations of a delivery system for delivering a medical device around an aorta, in accordance with an application of the present invention;

FIGS. 4A and 4B are cross-sectional views of the delivery system of FIGS. 3A-D, in accordance with an application of the present invention;

FIGS. 12A-C are cross-sectional schematic illustrations of another delivery system, in accordance with an application of the present invention;

FIGS. 15A-E are schematic illustrations of an extra-luminal ring, in accordance with an application of the present invention;

DETAILED DESCRIPTION OF APPLICATIONS

Figure 1D:
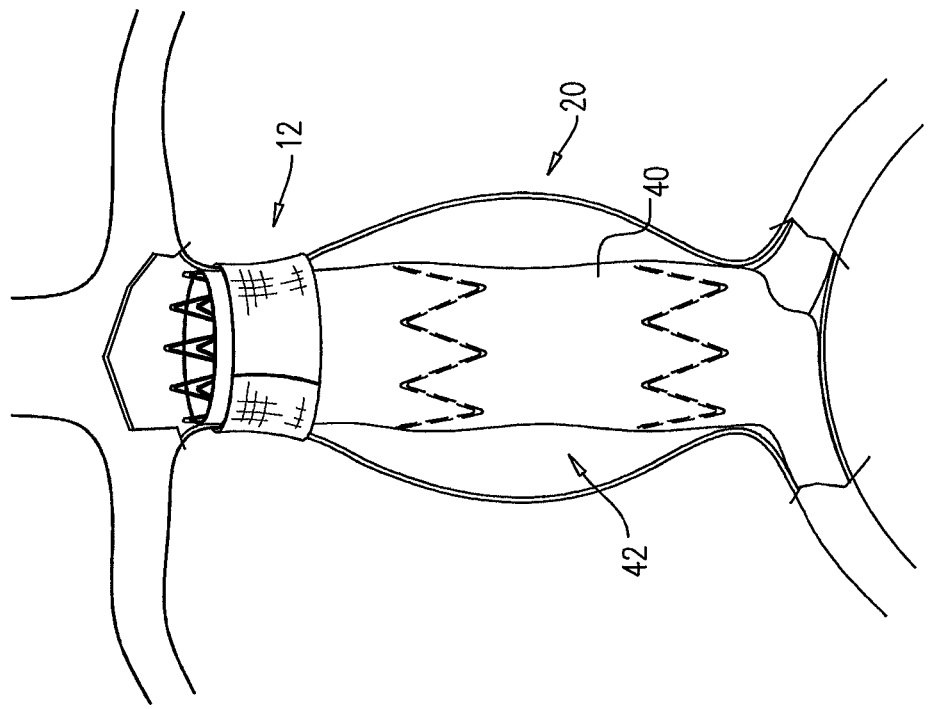

FIGS. 1A-D are schematic illustrations of a delivery system 10 for delivering a medical device 12 around an aorta 20, in accordance with an application of the present invention. Delivery system 10 may be used for delivering medical device 12 around aorta 20 (as shown) or other tissue, such as an organ, e.g., as a tubular organ, e.g., another blood vessel or a nerve. Delivery system 10 comprises a catheter 30, which comprises an outer pull-back shaft 32 having generally rectangular cross sections. Medical device 12 is initially removably disposed within outer pull-back shaft 32, with the medical device in a deformed generally planar state, as shown in FIG. 1A. For some applications, medical device 12 comprises an extra-luminal ring, such as shown in FIGS. 1A-D. For some of these applications, the ring is generally planar and rectangular when deformed for delivery.

During a first stage of an implantation procedure performed using delivery system 10, a surgeon creates a working channel, typically laparoscopically or hand-assisted laparoscopically, to an external surface of a portion of a target organ, such as aorta 20, e.g., a neck of an aneurysmal aorta, such as a sub-renal neck immediately inferior to the renal arteries, as shown in FIGS. 1A-D, or a supra-renal neck, an ascending aortic neck, or a neck adjacent the right subclavian artery (locations not shown). The surgeon advances a distal portion of delivery system 10 to the target organ, such as aorta 20, as shown in FIG. 1A. Typically, the surgeon advances a distal end 36 of outer pull-back shaft 32 slightly beyond the far side of the aorta, such that that outer pull-back shaft 32 is tangential to the aorta, as shown in FIG. 1A.

As shown in FIG. 1B, the surgeon subsequently proximally withdraws pull-back shaft 32, while simultaneously preventing proximal movement of medical device 12 using a stopper shaft. The stopper shaft is not shown in FIG. 1B; various configurations thereof are described in detail hereinbelow with reference to FIGS. 3A-14C. Withdrawal of the pull-back shaft deploys medical device 12 from distal end 36 of pull-back shaft 32. The medical device is configured to assume a curved shape upon deployment, and thus wraps around the organ, e.g., the aorta, as the device is deployed, as shown in FIG. 1B. Typically, the device is self-curling, and, to this end, typically comprises a shape memory material, such as a super-elastic metal, e.g., Nitinol, which is heat-set to assume the curled configuration, e.g., a circularly-, helically-, or spirally-bent configuration.

Figure 1C:
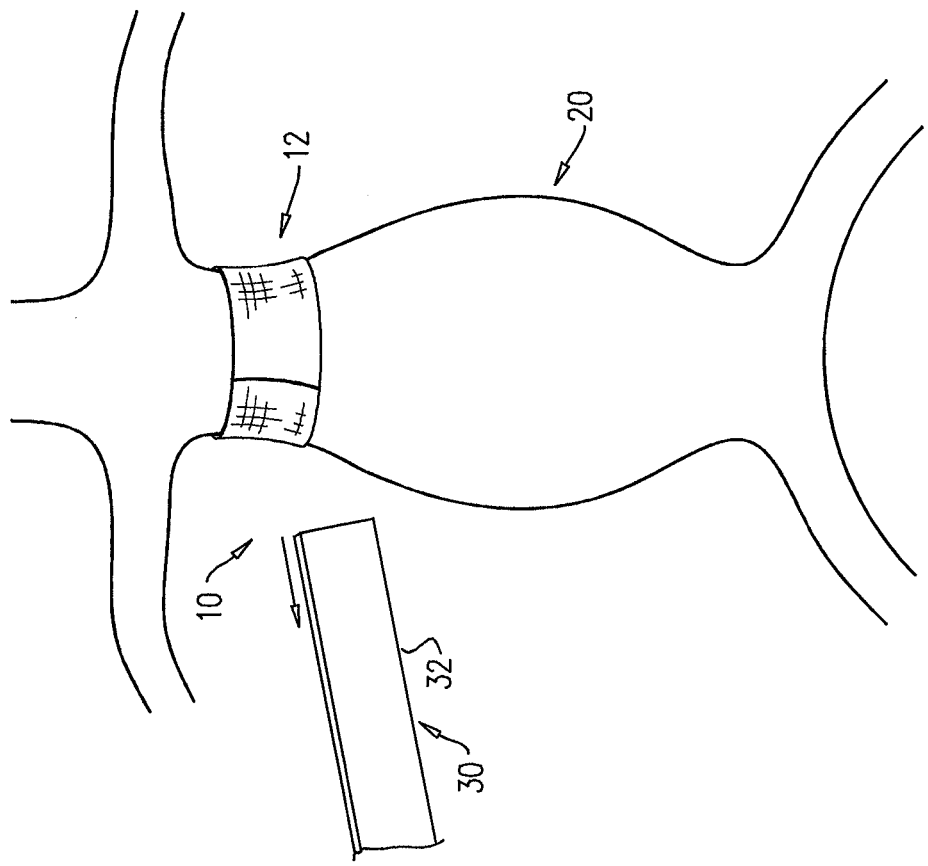

FIG. 1C shows pull-back shaft 32 and medical device 12 after the device has been fully deployed from the shaft. As can be seen, the device encircles at least a portion of the organ, e.g., the aorta, such as only a portion of or the entire organ.

When deployed around the neck of an aneurysmal aorta, medical device 12 creates a landing zone for an endovascular stent-graft 40 (which optionally is bifurcated, as shown). As shown in FIG. 1D, endovascular stent-graft 40 is deployed in the aorta, spanning an aneurysm 42 thereof. A distal portion of the stent-graft is positioned against the internal wall of the aorta at the landing zone. The landing zone provided by medical device 12 helps create a non-leaking seal between the stent-graft and the wall of the aorta. Medical device 12 thus helps secure the aneurismal neck from widening and/or leaking.

Alternatively, for some applications, endovascular stent-graft 40 is implanted first, and subsequently medical device 12 is placed around the aorta.

Figure 2A:
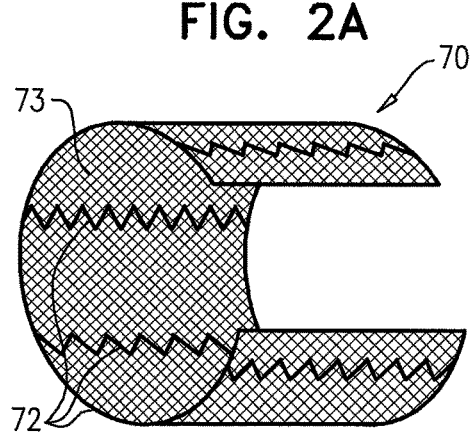
FIG. 2A is an isometric view of an extra-luminal ring, in accordance with an application of the present invention.

FIG. 2A is an isometric view of an extra-luminal ring 70, in accordance with an application of the present invention. For some applications, medical device 12, described hereinabove with reference to FIGS. 1A-D and hereinbelow with reference to FIGS. 3A-14C, comprises extra-luminal ring 70. Extra-luminal ring 70 comprises a structural member 72 and, optionally, a textile member 73, securely attached to and at least partially covering structural member 72 (typically an inner surface of the ring). Structural member 70 typically comprises a shape memory material, such as a super-elastic metal, e.g., Nitinol. Textile member 73 comprises an implantable-grade, biologically-compatible fabric, and may comprise, for example, a polyester, a polyethylene (e.g., a poly-ethylene-terephthalate), a polypropylene mesh, a polymeric film material (e.g., polytetrafluoroethylene), a polymeric textile material (e.g., woven polyethylene terephthalate (PET)), natural tissue graft (e.g., saphenous vein or collagen), or a combination thereof. For some applications, textile member 73 comprises a macroporous medical textile member mention, such as described in US Patent Application Publication 2010/0292774 to Shalev, which is assigned to the assignee of the present application and is incorporated herein by reference. Alternatively or additionally, extra-luminal ring 70 comprises an external microporous layer, such as described in the '774 publication.

Figure 2B:
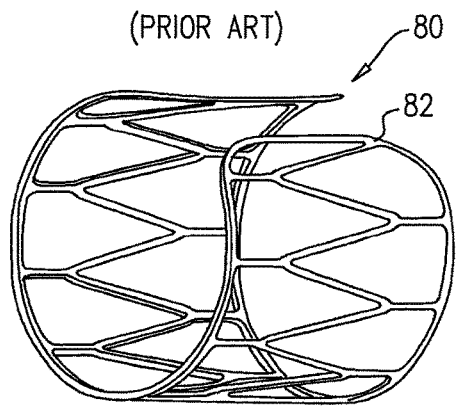
FIGS. 2B-D are schematic illustrations of another extra-luminal ring, as known in the prior art.
Figure 2C:
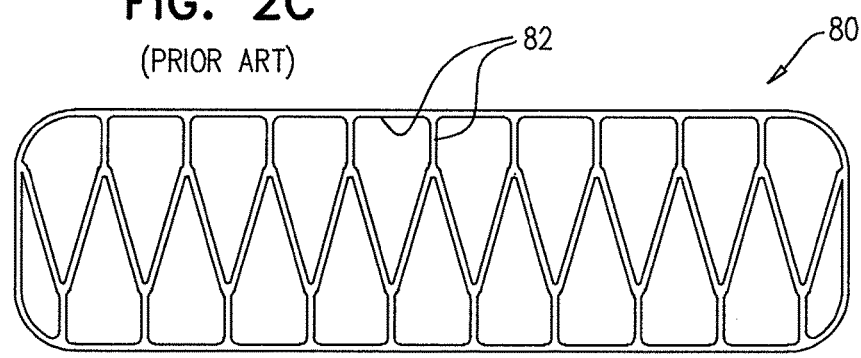
Figure 2D:
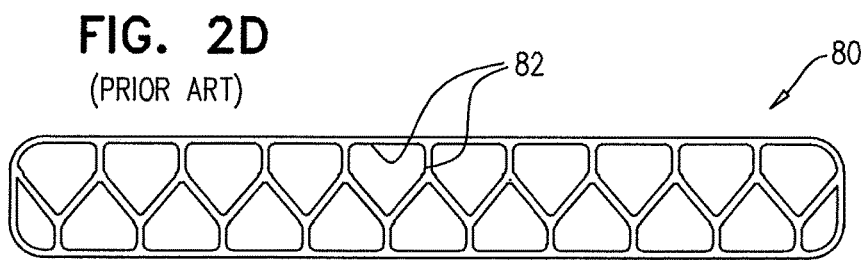

FIGS. 2B-D are schematic illustrations of another extra-luminal ring 80, as known in the prior art. Extra-luminal ring 80 is described in above-mentioned US Patent Application Publication 2010/0292774 to Shalev, with reference to FIGS. 9A-D thereof. FIG. 2B is an isometric view of extra-luminal ring 80 in a relaxed, generally cylindrical state. FIG. 7C shows extra-luminal ring 80 in a deformed planar state. For some applications, a length of extra-luminal ring 80 equals the circumference of both distal and proximal ends of extra-luminal ring 80 when in the relaxed, generally cylindrical state shown in FIG. 2B. FIG. 7D shows extra-luminal ring 80 in another deformed planar state, in which the ring has also been longitudinally deformed, such as in order to facilitate insertion of the ring into a laparoscopic channel.

For some applications of the present invention, medical device 12, described hereinabove with reference to FIGS. 1A-D and hereinbelow with reference to FIGS. 3A-14C, comprises extra-luminal ring 80. Extra-luminal ring 80 comprises a structural member 82 and, typically, a textile member (for clarity, not shown in FIGS. 2B-D). Structural member typically comprises a super-elastic metal, e.g., Nitinol. Typically, ring 80 is self-expanding. For some applications, when in a relaxed state, ring 80 is circularly bent, as shown in the figures. For other applications, when relaxed the ring is helically-bent or spirally-bent (configurations not shown).

Figure 3A:
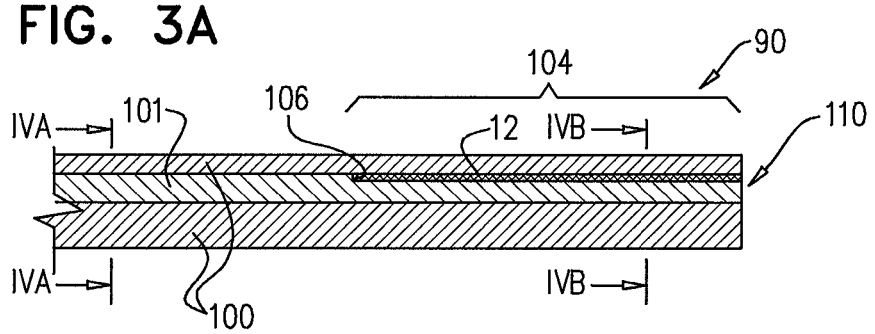
FIGS. 3A-D are cross-sectional views of a delivery system, in accordance with an application of the present invention.

FIG. 3A is a cross-sectional view of a delivery system 90, in accordance with an application of the present invention. Delivery system 90 is an exemplary implementation of delivery system 10, described hereinabove with reference to FIGS. 1A-D. Delivery system 90 comprises an outer pull-back shaft 100, a stopper shaft 101, and medical device 12 (e.g., an extra-luminal ring, such as ring 70 or ring 80) disposed therebetween in a distorted, planar state, at a distal end 110 of the delivery system. As can be seen in FIG. 3A, a distal portion 104 of stopper shaft 101 runs alongside medical device 12. Stopper shaft 101 is shaped so as to define a step 106 at a distal end of portion 104, which step serves to prevent proximal movement of medical device 12 as outer pull-back shaft 100 is proximally withdrawn during deployment of the medical device.

Figure 3B:
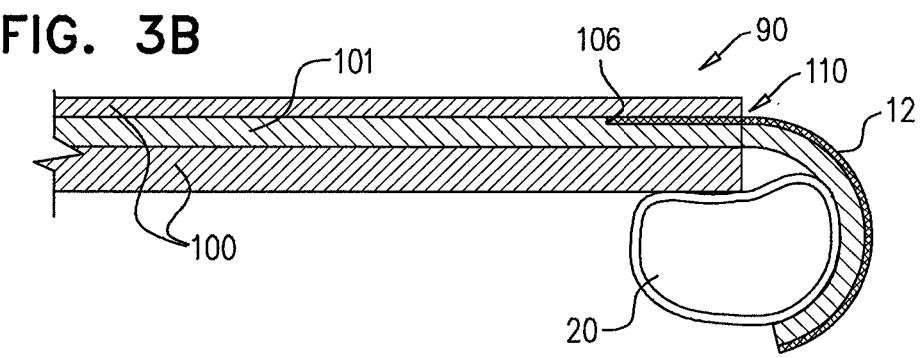
Figure 3C:
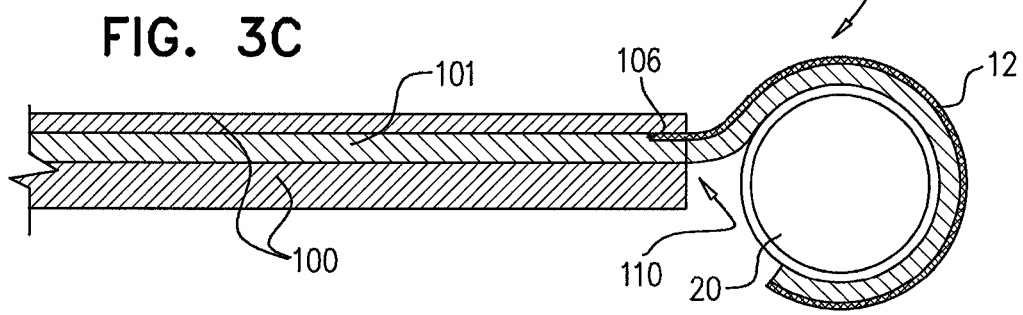
Figure 3D:
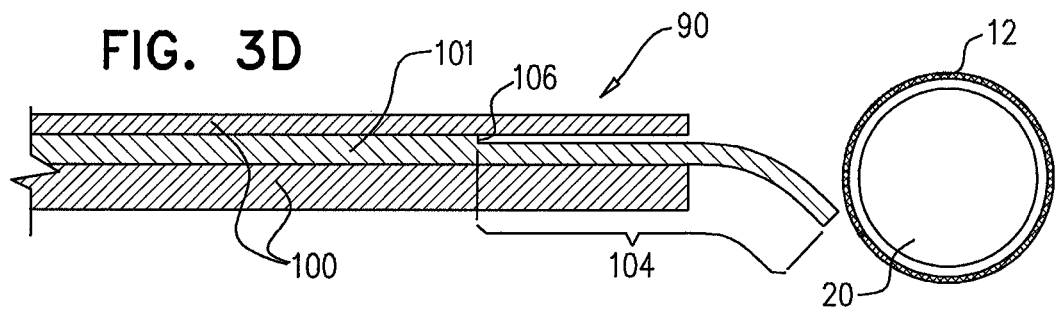

FIGS. 3B-D are schematic cross-sectional views of delivery system 90 showing the deployment of medical device 12 around aorta 20, in accordance with an application of the present invention. During a deployment procedure, distal end 110 of delivery system 90 is advanced beyond aorta 20, as described hereinabove with reference to FIG. 1A. Outer pull-back shaft 100 is proximally withdrawn, while stopper shaft 101 is held in place. As a result, medical device 12 and distal portion 104 of stopper shaft 101 are deployed from outer pull-back shaft 100, and curl around a portion of aorta 20, as shown in FIG. 3B. Distal portion 104 of stopper shaft 101 protects aorta 20 from any traumatic/sharp features (e.g. small metal strut elements) of medical device 12 as the medical device is deployed around the aorta.

The proximal withdrawal of outer pull-back shaft 100 continues, as shown in FIG. 3C, until the outer pull-back shaft has been completely withdrawn from medical device 12, as shown FIG. 3D.

Reference is made to FIGS. 4A and 4B, which are schematic cross-sectional views of delivery system 90 and medical device 12 along lines IVA-IVA and IVB-IVB of FIG. 3A, respectively, in accordance with an application of the present invention. As can be seen in these views, delivery system 90 has generally rectangular cross-sections.

Figure 5:
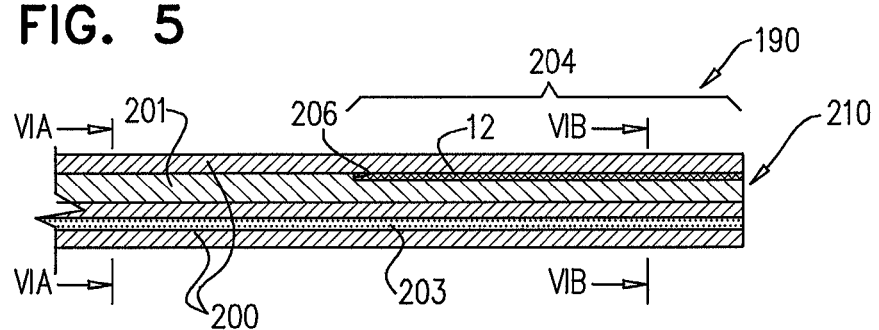
FIGS. 5 and 6A-B are cross-sectional schematic illustrations of another delivery system, in accordance with an application of the present invention.
Figure 6A:
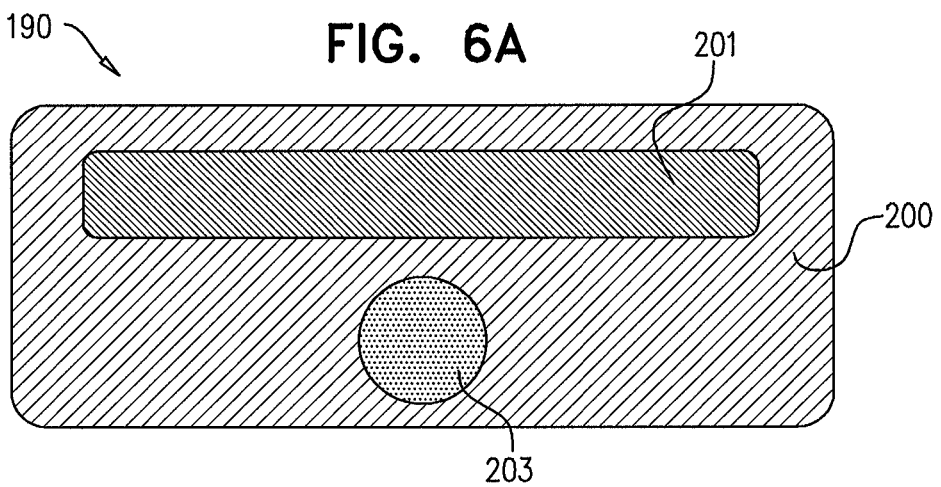
Figure 6B:
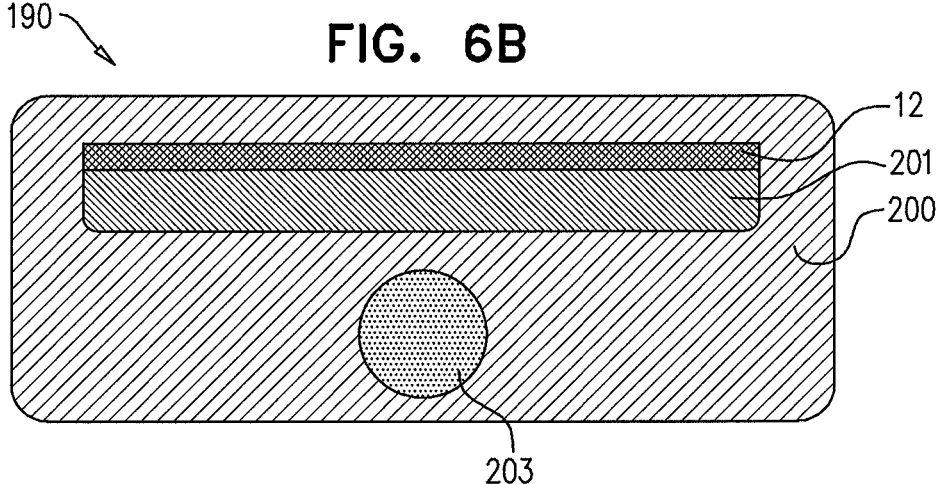

Reference is now made to FIGS. 5 and 6A-B, which are schematic cross-sectional views of another delivery system 190, in accordance with an application of the present invention. FIGS. 6A and 6B are schematic cross-sectional views of delivery system 190 and medical device 12 along lines VIA-VIA and VIB-VIB of FIG. 5, respectively. As can be seen in the views of FIGS. 6A and 6B, delivery system 190 has generally rectangular cross sections. Delivery system 190 is an exemplary implementation of delivery system 10, described hereinabove with reference to FIGS. 1A-D. Except as described below, delivery system 190 is generally similar to delivery system 90, described hereinabove with reference to FIGS. 3A-D and 4A-B. Delivery system 90 comprises an outer pull-back shaft 200, a stopper shaft 201, and medical device 12 (e.g., an extra-luminal ring, such as ring 70 or ring 80) disposed therebetween in a distorted, planar state, at a distal end 210 of the delivery system. As can be seen in FIG. 5, a distal portion 204 of stopper shaft 201 runs alongside medical device 12. Stopper shaft 201 is shaped so as to define a step 206 at a distal end of portion 204, which step serves to prevent proximal movement of medical device 12 as outer pull-back shaft 200 is proximally withdrawn during deployment of the medical device.

As shown in FIGS. 5 and 6A-B, outer pull-back shaft 200 is shaped so as to define a generally circular guide lumen 203 therethrough. A guidewire (alternatively, a guiding rod; not shown) is introduced through the guide lumen during an implantation procedure. For example, the guidewire may comprise a stainless-steel or a Nitinol spring.

Figure 7A:
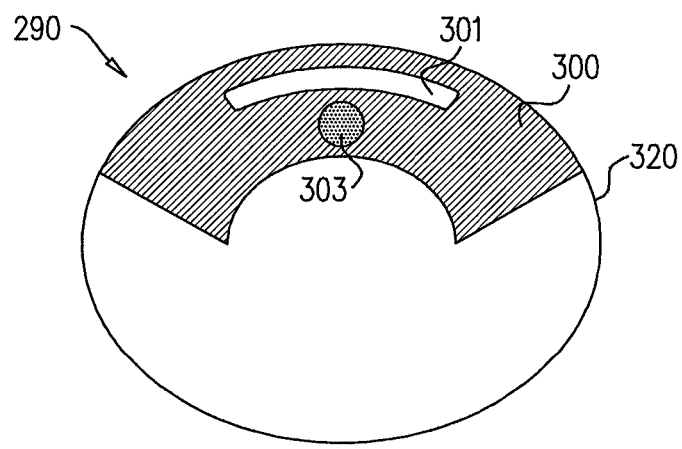
FIGS. 7A-B are cross-sectional schematic illustrations of yet another delivery system, in accordance with an application of the present invention.
Figure 7B:
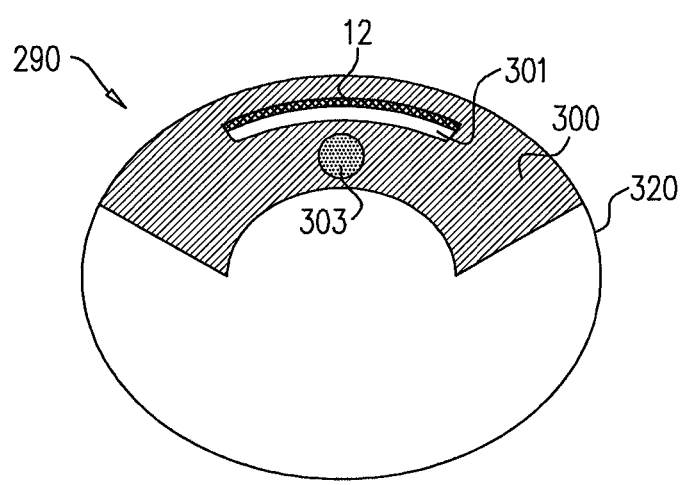

Reference is now made to FIGS. 7A and 7B, which are cross-sectional schematic illustrations of yet another delivery system 290, in accordance with an application of the present invention. Delivery system 290 is an exemplary implementation of delivery system 10, described hereinabove with reference to FIGS. 1A-D. Except as described below, delivery system 290 is generally similar to delivery system 190, described hereinabove with reference to FIGS. 5 and 6A-B. The delivery system and medical device have been inserted into a cylindrical laparoscopic working channel 320. Delivery system 290 comprises an outer pull-back shaft 300, a stopper shaft 301, and medical device 12 (e.g., an extra-luminal ring, such as ring 70 or ring 80). Outer pull-back shaft 300, stopper shaft 301, and medical device 12 are bent around a central longitudinal axis of working channel 320, at a distal end thereof. A distal portion of stopper shaft 301 runs alongside medical device 12 (not shown in FIGS. 7A and 7B, but similar to the configuration shown in FIGS. 3A and 5). Stopper shaft 301 is shaped so as to define a step at a distal end of the distal portion, which step serves to prevent proximal movement of medical device 12 as outer pull-back shaft 300 is proximally withdrawn during deployment of the medical device. Upon deployment from working channel 320, outer pull-back shaft 300, stopper shaft 301, and medical device 12 straighten in the short dimension (around the axis of the working channel), and curl in the long dimension (similar to the curling shown in FIG. 3B).

Figure 8:
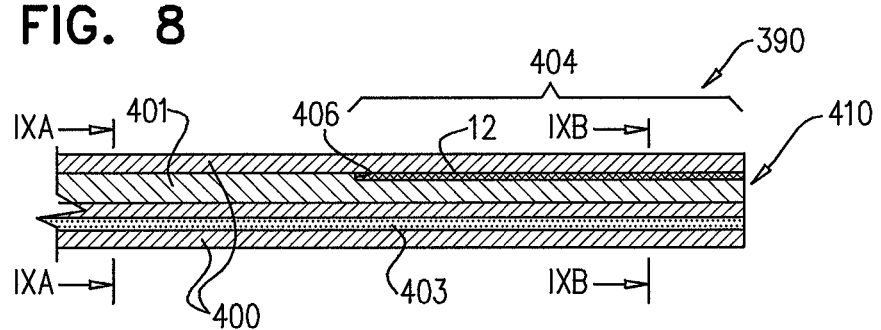
FIGS. 8 and 9A-B are cross-sectional schematic illustrations of another delivery system, in accordance with an application of the present invention.
Figure 9A:
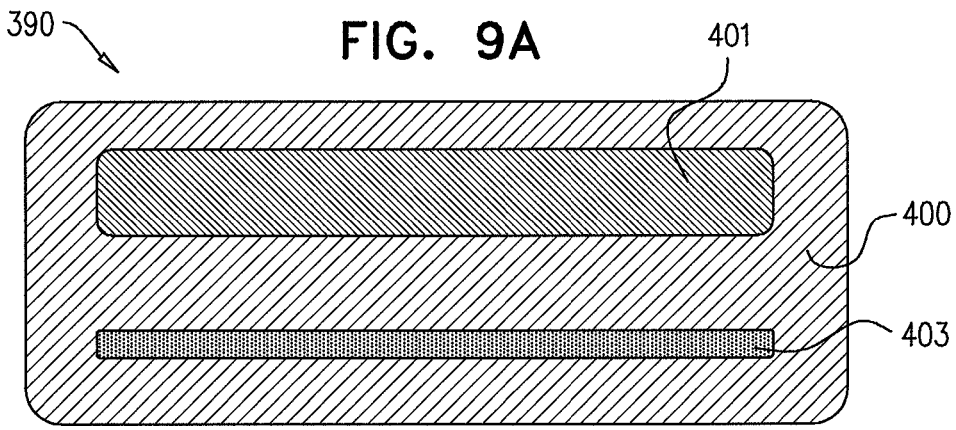
Figure 9B:
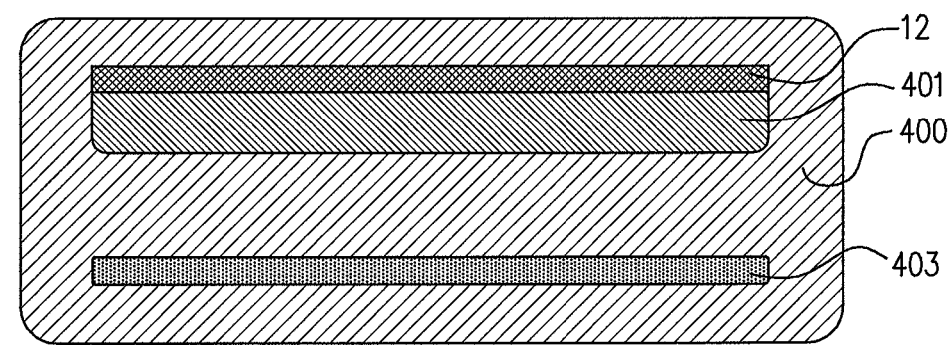

As shown in FIGS. 7A-B, outer pull-back shaft 300 is shaped so as to define a generally circular guide lumen 303 therethrough. A guidewire or a guiding rod (not shown) is introduced through the guide lumen during an implantation procedure. For example, the guidewire may comprise a stainless-steel or a Nitinol spring Reference is now made to FIGS. 8 and 9A-B, which are schematic cross-sectional views of another delivery system 390, in accordance with an application of the present invention. FIGS. 9A and 9B are schematic cross-sectional views of delivery system 390 and medical device 12 along lines IXA-IXA and IXB-IXB of FIG. 8, respectively. Delivery system 390 is an exemplary implementation of delivery system 10, described hereinabove with reference to FIGS. 1A-D. As can be seen in the views of FIGS. 9A and 9B, delivery system 390 has generally rectangular cross sections. Delivery system 390 comprises an outer pull-back-shaft 400, a stopper shaft 401, and medical device 12 (e.g., an extra-luminal ring, such as ring 70 or ring 80) disposed therebetween in a distorted, planar state, at a distal end 410 of the delivery system. As can be seen in FIG. 8, a distal portion 404 of stopper shaft 401 runs alongside medical device 12. Stopper shaft 401 is shaped so as to define a step 406 at a distal end of portion 404, which step serves to prevent proximal movement of medical device 12 as outer pull-back shaft 400 is proximally withdrawn during deployment of the medical device.

As shown in FIGS. 8 and 9A-B, outer pull-back shaft 400 is shaped so as to define a thin rectangular guide lumen 403. A ribbon-shaped guide member (such as guide member 508 or 608, described hereinbelow with reference to FIGS. 10A and 11A, respectively) is introduced through the guide lumen during an implantation procedure. For example, the guide member may comprise a steel spring. Alternatively, the ribbon-shaped guide member is initially introduced to and partially around the aorta and over it, and the guide lumen is introduced and pushed distally to the aorta.

Figure 10A:
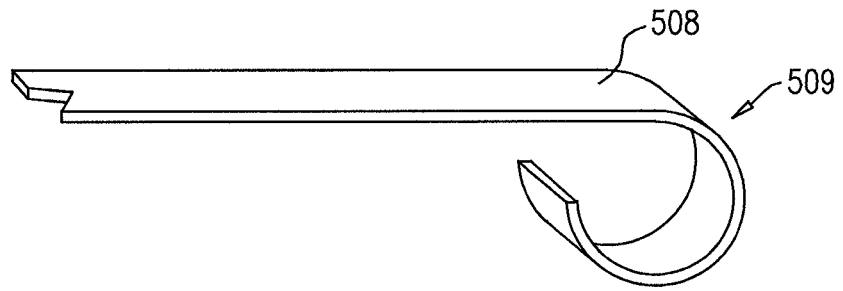
FIG. 10A is a schematic illustration of a ribbon-shaped guide member, in accordance with an application of the present invention.

Reference is now made to FIG. 10A, which is a schematic illustration of a ribbon-shaped guide member 508, in accordance with an application of the present invention. When in a relaxed state, ribbon-shaped guide member 508 has a pre-bent distal end 509, e.g., circularly pre-bent (as shown), helically pre-bent (configuration not shown), or spirally pre-bent (configuration not shown). Ribbon-shaped guide member 508 typically comprises a shape memory material, such as a super-elastic metal, e.g., Nitinol, which is heat-set to assume the bent configuration.

Figure 10B:
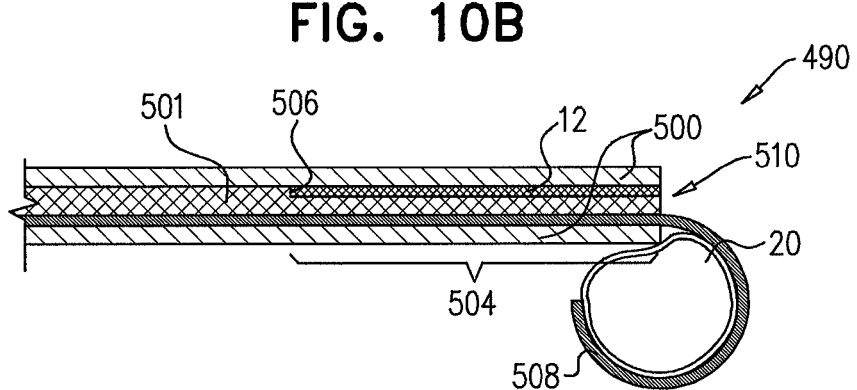
FIGS. 10B-C are schematic cross-sectional illustrations of yet another delivery system, in accordance with an application of the present invention.
Figure 10C:
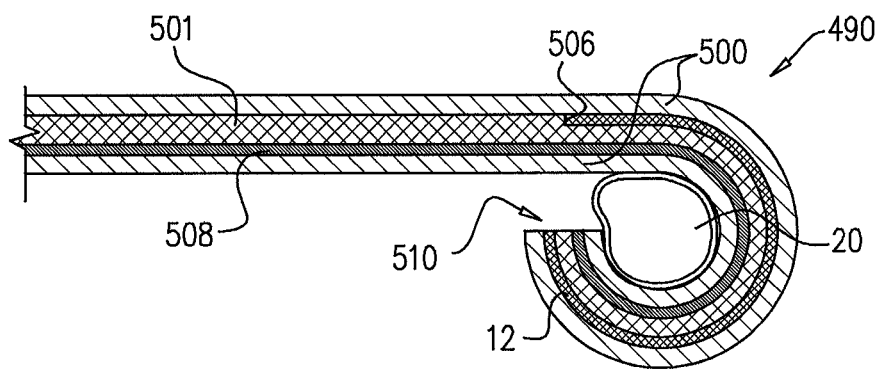

Reference is made to FIGS. 10B-C, which are schematic cross-sectional illustrations of yet another delivery system 490, in accordance with an application of the present invention. Delivery system 490 is an exemplary implementation of delivery system 10, described hereinabove with reference to FIGS. 1A-D. Delivery system 490 comprises an outer pull-back shaft 500, a stopper shaft 501, and medical device 12 (e.g., an extra-luminal ring, such as ring 70 or ring 80) disposed therebetween in a distorted, planar state, at a distal end 510 of the delivery system. As can be seen in FIGS. 10B-C, a distal portion 504 of stopper shaft 501 runs alongside medical device 12. Stopper shaft 501 is shaped so as to define a step 506 at a distal end of portion 504, which step serves to prevent proximal movement of medical device 12 as outer pull-back shaft 500 is proximally withdrawn during deployment of the medical device.

Delivery system further comprises ribbon-shaped guide member 508, described hereinabove with reference to FIG. 10A. During an implantation procedure, a delivery tube (not shown) holds guide member 508 in a flat, non-bent state, as the guide member is introduced. Optionally, the entire delivery system, including pull-back shaft 500, is placed in the delivery tube. Upon reaching the tubular organ, e.g., aorta 20, the guide member is pushed out of the distal end of the delivery tube, and curls around the tubular organ, e.g., aorta 20, as shown in FIG. 10B.

As shown in FIG. 10C, pull-back shaft 500, stopper shaft 501, and medical device 12 are advanced distally over ribbon-shaped guide member 508, around aorta 20. Guide member 508 guides the pull-back shaft, stopper shaft, and medical device around the aorta, such that distal end portions of the pull-back shaft and stopper shaft conform with the bent shape of guide member 508. The distal portion of delivery system 490 thus assumes the shape of the distal end of guide member 508 when the distal end of the guide member is inside the distal portion pull-back shaft 500, and resumes its relaxed shape when the distal end of guide member is proximally removed from the distal end of pull-back shaft 500.

Thereafter (not shown), outer pull-back shaft 500 is proximally withdrawn, while stopper shaft 501 is held in place. As a result, medical device 12 and distal portion 504 of stopper shaft 501 are deployed from outer pull-back shaft 500, and curl around a portion of aorta 20. Distal portion 504 of stopper shaft 501 protects aorta 20 from any metal elements of medical device 12 as the medical device is deployed around the aorta. The proximal withdrawal of outer pull-back shaft 500 continues, until the outer pull-back shaft has been completely withdrawn from medical device 12.

Figure 11A:
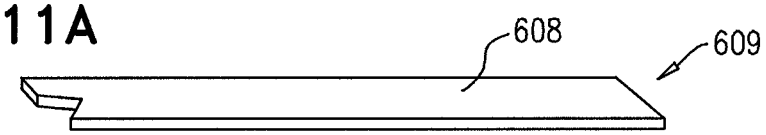
FIG. 11A is a schematic illustration of another ribbon-shaped guide member, in accordance with an application of the present invention.

Reference is made to FIG. 11A, which is a schematic illustration of a ribbon-shaped guide member 608, which has a straight, flat, and stiff distal end 609, in accordance with an application of the present invention. For example, the guide member may comprise a stainless-steel or a Nitinol wire, or a rod.

Figure 11B:
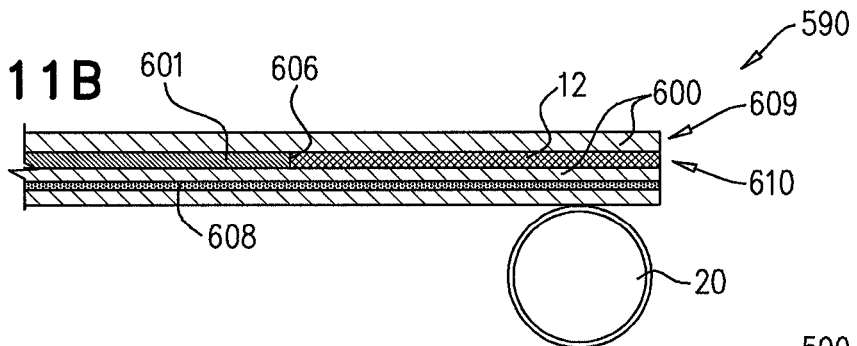
FIGS. 11B-D are schematic cross-sectional illustrations of yet another delivery system, in accordance with an application of the present invention.
Figure 11C:
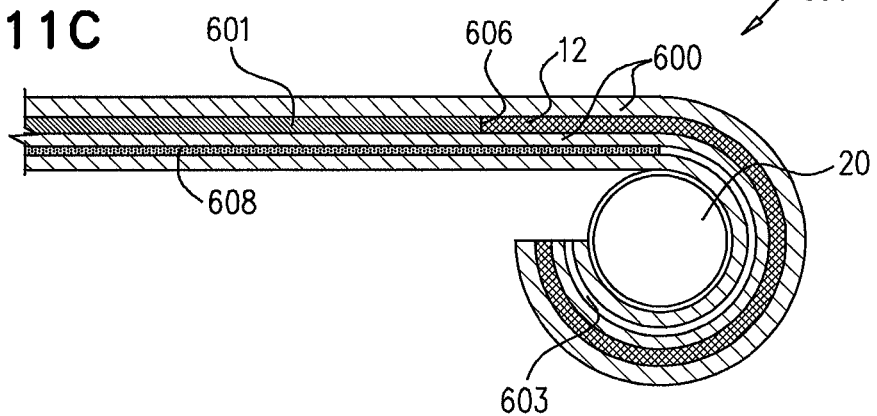
Figure 11D:
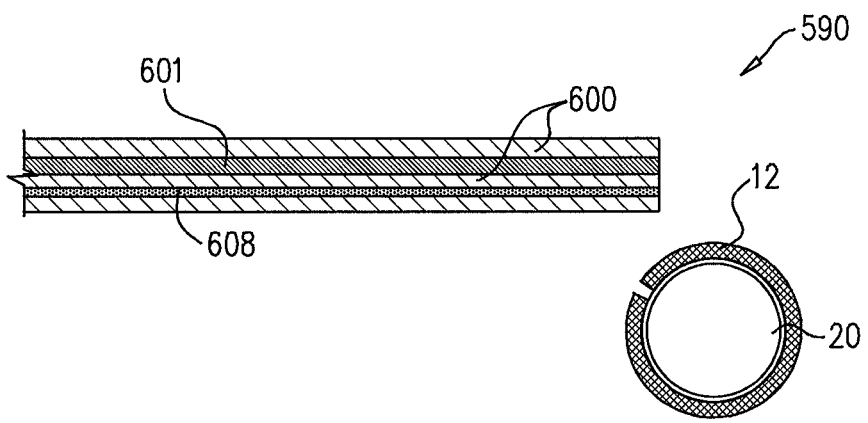

Reference is made to FIGS. 11B-D, which are schematic cross-sectional illustrations of yet another delivery system 590, in accordance with an application of the present invention. Delivery system 590 is an exemplary implementation of delivery system 10, described hereinabove with reference to FIGS. 1A-D. Delivery system 590 comprises an outer pull-back shaft 600, a stopper shaft 601, and medical device 12 (e.g., an extra-luminal ring, such as ring 70 or ring 80) disposed therebetween in a distorted, planar state, at a distal end 610 of the delivery system. For some applications, a distal end of stopper shaft 601 abuts a proximal end of medical device 12, so as to prevent proximal movement of medical device 12 as outer pull-back shaft 600 is proximally withdrawn during deployment of the medical device.

Delivery system further comprises ribbon-shaped guide member 608, described hereinabove with reference to FIG. 11A. During an implantation procedure, delivery system 590 is advanced to a tubular organ, e.g., aorta 20, and held tangential to the aorta, as shown in FIG. 11B. Flat, stiff distal end 609 of guide member 608 holds medical device 12 in a flat, non-bent state.

As shown in FIG. 11C, outer pull-back shaft 600, stopper shaft 601, and medical device 12 are further distally advanced, while guide member 608 is held in place. (A distal portion of a lumen 603 in which stopper shaft 601 is positioned is vacated during this advancement.) The shape memory of medical device 12 causes the medical device to curve around aorta 20 as the medical device advances beyond distal end 609 of guide member 608 and the medical device assumes its relaxed state. Pull-back shaft 600 is sufficiently flexible, and the spring constant of medical device 12 is sufficiently high, that medical device implant 12 enforces its curvature on pull-back shaft 600, and thus guides the pull-back shaft around the aorta. Pull-back shaft 600 thus has a relaxed state that is affected by mechanical and geometric characteristics of medical device 12.

After medical device 12 has been curled around aorta 20, pull-back shaft 600 and stopper shaft 601 are proximally withdrawn over ribbon-shaped guide member 608, leaving the medical device implanted around the aorta.

Reference is now made to FIGS. 12A-C, which are schematic cross-sectional views of another delivery system 890, in accordance with an application of the present invention. FIGS. 12B and 12C are schematic cross-sectional views of delivery system 890 and medical device 12 along lines XIIB-XIIB and XIIC-XIIC of FIG. 12A, respectively. As can be seen in the views of FIGS. 12B and 12C, delivery system 890 has generally rectangular cross sections. Delivery system 890 is an exemplary implementation of delivery system 10, described hereinabove with reference to FIGS. 1A-D. Except as described below, delivery system 890 is generally similar to delivery system 390, described hereinabove with reference to FIGS. 9A-C. Delivery system 890 comprises an outer pull-back shaft 900, a stopper shaft 901, and medical device 12 (e.g., an extra-luminal ring, such as ring 70 or ring 80) disposed therebetween in a distorted, planar state, at a distal end 910 of the delivery system. As can be seen in FIG. 12A, a distal end of stopper shaft 901 abuts a proximal end of medical device 12, so as to prevent proximal movement of medical device 12 as outer pull-back shaft 900 is proximally withdrawn during deployment of the medical device.

As shown in FIGS. 12A-C, outer pull-back shaft 900 is shaped so as to define a thin rectangular guide lumen 903. A ribbon-shaped guide member (such as guide member 508 or 608) is introduced through the guide lumen during an implantation procedure.

Figure 13A:
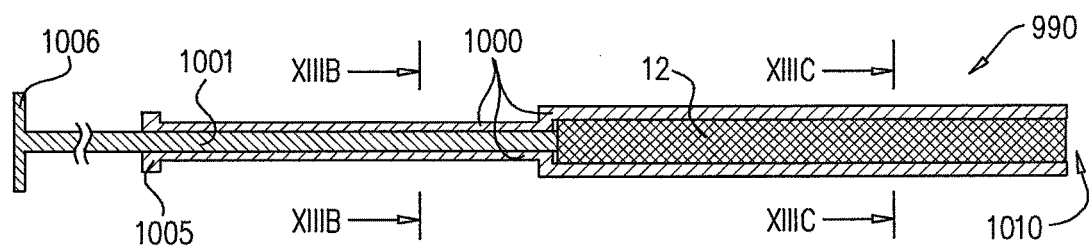
FIGS. 13A-C are cross-sectional schematic illustrations of still another delivery system, in accordance with an application of the present invention.
Figure 13B:
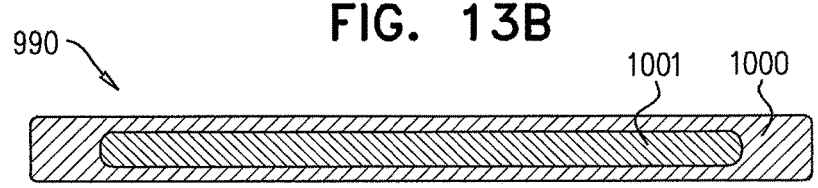
Figure 13C:
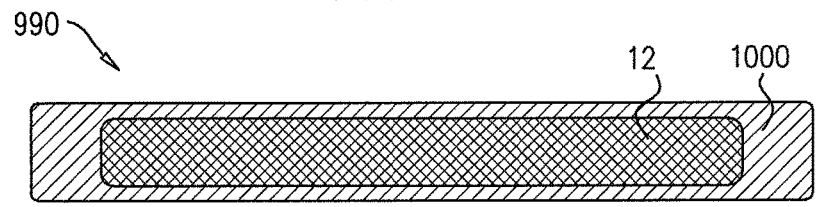

Reference is now made to FIGS. 13A-C, which are schematic cross-sectional views of still another delivery system 990, in accordance with an application of the present invention. FIGS. 13B and 13C are schematic cross-sectional views of delivery system 990 and medical device 12 along lines XIIIB-XIIIB and XIIIC-XIIIC of FIG. 13A, respectively. As can be seen in the views of FIGS. 13B and 13C, delivery system 990 has generally rectangular cross sections. Delivery system 990 is an exemplary implementation of delivery system 10, described hereinabove with reference to FIGS. 1A-D. Except as described below, delivery system 990 is generally similar to delivery system 90, described hereinabove with reference to FIGS. 3A-D and 4A-B. Delivery system 990 comprises an outer pull-back shaft 1000, a stopper shaft 1001, and medical device 12 (e.g., an extraluminal ring, such as ring 70 or ring 80) disposed therebetween in a distorted, planar state, at a distal end 1010 of the delivery system. As can be seen in FIG. 13A, a distal end of stopper shaft 1001 abuts a proximal end of medical device 12, so as to prevent proximal movement of medical device 12 as outer pull-back shaft 1000 is proximally withdrawn during deployment of the medical device.

As can be seen in FIG. 13A-C, delivery system 990 (and outer pull-back shaft 1000) has a larger cross-sectional area near distal end 1010, in order to contain medical device 12, than at a more proximal region, in which the narrower stopper shaft 1001 is contained. For some applications, a proximal portion of the pull-back shaft 1000 is shaped so as to define an anti-slip surface pattern 1005. For some applications, a proximal end of stopper shaft 1001 comprises or is shaped so as to define a handle 1006.

Figure 14A:
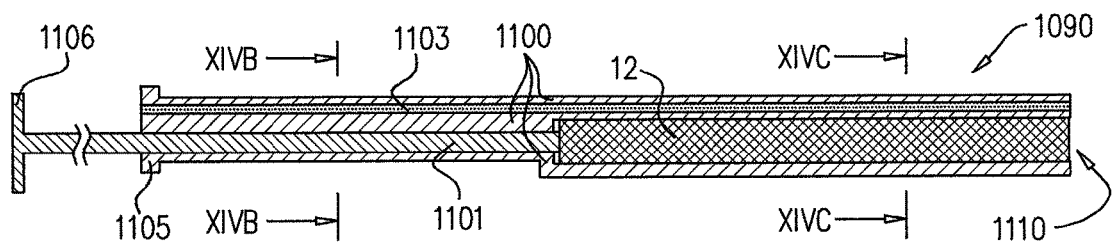
FIGS. 14A-C are cross-sectional schematic illustrations of another delivery system, in accordance with an application of the present invention.
Figure 14B:
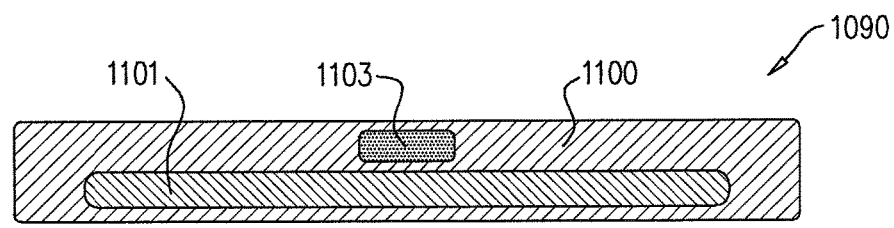
Figure 14C:
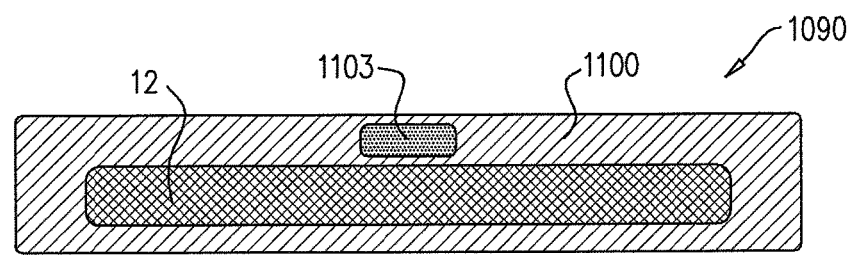

Reference is now made to FIGS. 14A-C, which are schematic cross-sectional views of another delivery system 1090, in accordance with an application of the present invention. FIGS. 14B and 14C are schematic cross-sectional views of delivery system 1090 and medical device 12 along lines XIVB-XIVB and XIVC-XIVC of FIG. 14A, respectively. As can be seen in the views of FIGS. 14B and 14C, delivery system 990 has generally rectangular cross sections. Delivery system 1090 is an exemplary implementation of delivery system 10, described hereinabove with reference to FIGS. 1A-D. Except as described below, delivery system 1090 is generally similar to delivery system 90, described hereinabove with reference to FIGS. 3A-D and 4A-B. Delivery system 1090 comprises an outer pull-back shaft 1100, a stopper shaft 1101, and medical device 12 (e.g., an extra-luminal ring, such as ring 70 or ring 80) disposed therebetween in a distorted, planar state, at a distal end 1110 of the delivery system. As can be seen in FIG. 14A, a distal end of stopper shaft 1101 abuts a proximal end of medical device 12, so as to prevent proximal movement of medical device 12 as outer pull-back shaft 1100 is proximally withdrawn during deployment of the medical device.

As shown in FIGS. 14A-C, outer pull-back shaft 1100 is shaped so as to define a guide lumen 1103 therethrough. A guidewire (not shown) is introduced through the guide lumen during an implantation procedure. For example, the guidewire may comprise a steel a stainless-steel or a Nitinol wire, or a rod.

As can be seen in FIG. 14A-C, delivery system 1090 (and outer pull-back shaft 1100) has a larger cross-sectional area near distal end 1110, in order to contain medical device 12, than at a more proximal region, in which the narrower stopper shaft 1101 is contained. For some applications, a proximal portion of the pull-back shaft 1100 is shaped so as to define an anti-slip surface pattern 1105. For some applications, a proximal end of stopper shaft 1101 comprises or is shaped so as to define a handle 1106. For some applications, handle 1106 is shaped so as to define a small opening 1109, in order to accommodate the insertion and removal of a guide wire or ribbon-shaped guide member (the guide wire and ribbon-shaped guide member are not shown in the figure; the ribbon-shaped guide member may be implemented as guide member 508 or 608).

Reference is again made to FIGS. 3A-4B, 5-6B, 7A-B, 8-9B, 10A-C, 11A-C, 12A-C, 13A-C, and 14A-C. For some applications, stopper shafts 101, 201, 301, 401, 501, 601, 901, 1001, and 1101 comprise a material that is axially non-compressible. For some applications, the material is flexible. Alternatively or additionally, for some applications, the stopper shafts instead or additionally comprises a shape memory material is that is configured to assume a curled shape when relaxed, and thus helps to curl medical device 12 around the tubular organ, e.g., the aorta. For some of the applications described with reference to FIGS. 3A-4B, 5-6B, 7A-B, 8-9B, and 10A-C, the stopper shaft extends only to, and abuts, a proximal end of medical device 12, rather than the distal end thereof as shown in these figures. Alternatively, for some of the applications described with reference to FIGS. 3A-4B, 5-6B, 7A-B, 8-9B, and 10A-C, the stopper shaft extends only a portion of medical device 12, rather than to the distal end thereof as shown in these figures.

Reference is now made to FIGS. 15A-E, which are schematic illustrations of an extra-luminal ring 1200, in accordance with an application of the present invention. FIGS. 15A-E show extra-luminal ring 1200 in different shapes, as described in detail hereinbelow. Extra-luminal ring 1200 comprises a structural member 1202. Structural member 1202 typically comprises a plurality of stent struts 1204, which are typically interconnected with one another. Typically, structural member 1202 comprises a shape memory material, such as Nitinol.

Figure 15A:
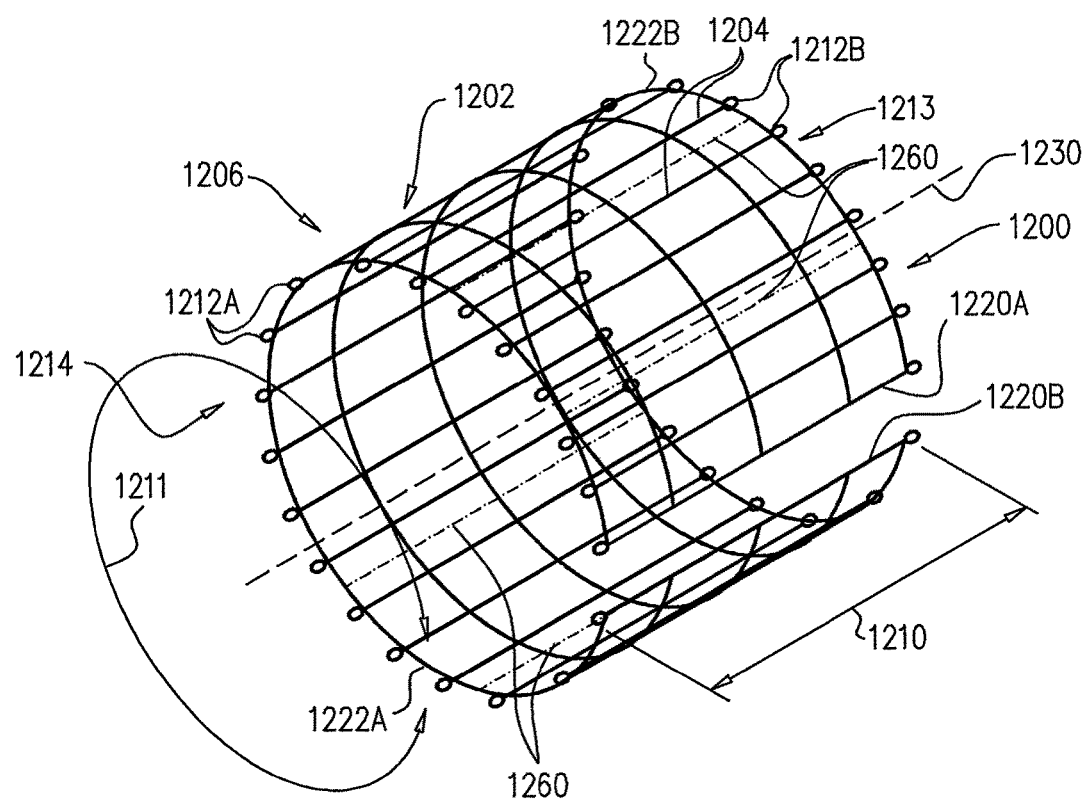

As shown in FIG. 15A, structural member 1202 is configured to assume a first elongate hollow shape 1206 when in a relaxed state. For example, first elongate hollow shape 1206 may be generally cylindrical, as shown. Extra-luminal ring 1200 is suitable for being placed around a tubular organ, e.g., aorta 20, and partially or completely surrounding the organ when the ring has first elongate hollow shape 1206 in the relaxed state. For applications in which structural member 1202 comprises a shape memory material, such as Nitinol, the material is typically heat-set to assume first elongate hollow shape 1206 when relaxed.

For some applications, as shown in FIG. 15B, structural member 1202, when deformed to a planar state 1208, generally defines a planar shape 1209 having two first sides 1220A and 1220B parallel to each other, and two second sides 1222A and 1222B parallel to each other. (It is noted that structural member 1202 is not necessarily deformed to planar state 1208 before, during, or after implantation; the planar state is described in order to illustrate certain geometric properties of the structural member.) For example, planar shape 1209 may be a parallelogram, e.g., a rectangle (as shown). The corners of planar shape 1209 may define right angles (as shown), or may be rounded (configuration not shown). For some applications, when structural member 1202 is deformed to planar state 1208, stent struts 1204 are arranged such that a first portion of stent struts 1204 are parallel to two first sides 1220A and 1220B, and a second portion of stent struts 1204 are parallel to two second sides 1222A and 1222B. Alternatively, the stent struts may be arranged diagonally with respect to sides 1222A and 1222B, or in another configuration (e.g., serpentine) (configurations not shown). Alternatively, for other applications, planar shape 1209 may be another non-parallelogram shape, such as a rhombus (configuration not shown).

For some applications, a length 1211 of each of two second sides 1222A and 1222B, when structural member 1202 is in planar state 1208 as shown in FIG. 15B, is equal to a circumference 1211 of structural member 1202, when structural member 1202 is in the relaxed state as shown in FIG. 15A. For some applications, length/circumference 1211 is at least 6 cm, no more than 15 cm, and/or between 6 and 15 cm.

For some applications, when in the relaxed state, as shown in FIG. 15A, structural member 1202 is configured such that (i) two first sides 1220A and 1220B are generally straight and parallel with each other, and (ii) two second sides 1222A and 1222B are curved at least partially around a first longitudinal axis 1230 defined by first elongate hollow shape 1206. For some applications, two sides 1222A and 1222B are parallel with first longitudinal axis 1230 (as shown); alternatively, the two sides are not parallel with the first longitudinal axis, such as when planar shape 1209 is a rhombus (configuration not shown). In addition, when in the relaxed state, as shown in FIG. 15A, structural member 1202 has proximal and distal ends 1213 and 1214, an axial length 1210, and relaxed circumference 1211 of either proximal end 1213 and/or distal end 1214 (the circumference does not include the longitudinal straight edges, i.e., first and second sides 1220A and 1220B). For some applications, axial length 1210 (e.g., the length of each of first sides 1220A and 1220B) is at least 1 cm, no more than 4 cm, and/or between 1 and 4 cm).

For some applications, when structural member 1202 is in planar state 1208 as shown in FIG. 15B, a ratio of (a) a length 1211 of each of two second sides 1222A and 1222B to (b) length 1210 of each of two first sides 1220A and 1220B is at least 2:1, such as at least 2.5:1, e.g., at least 3:1 or at least 4:1, e.g., at least 6:1. In general, this ratio equals the ratio of (a) the circumference (and diameter) of structural member 1202 when it has first elongate hollow shape 1206 in the relaxed state to (b) the circumference (and diameter) of structural member 1202 when it has second elongate hollow shape 1240 in the deformed state (without taking into account any additional possible radial compression of the structural member that may be imposed by an external delivery shaft, a releasable confining sheath, an elongate latching member, or other constraining element in which the structural member may be disposed). As a result, the deformation of structural member 1202 from the relaxed state to the deformed state for delivery typically substantially reduces the crossing profile of the structural member, which enables the use of a narrower delivery shaft, relative to the diameter of the device in its indicated geometrical dimensions, around the aorta.

For some applications, as shown in FIG. 15A, first elongate hollow shape 1206 assumed by structural member 1202 when in the relaxed state is that of a partial elongate hollow structure (e.g., a cylinder) that subtends an arc of less than 360 degrees. For these applications, two first sides 1220A and 1220B do not touch each other in the relaxed state. For other applications, first generally cylindrical shape 1206 assumed by structural member 1202 when in the relaxed state is circumferentially complete, e.g., that of complete cylinder (configuration not shown). For these applications, two first sides 1220A and 1220B touch each other in the relaxed state.

Figure 15D:
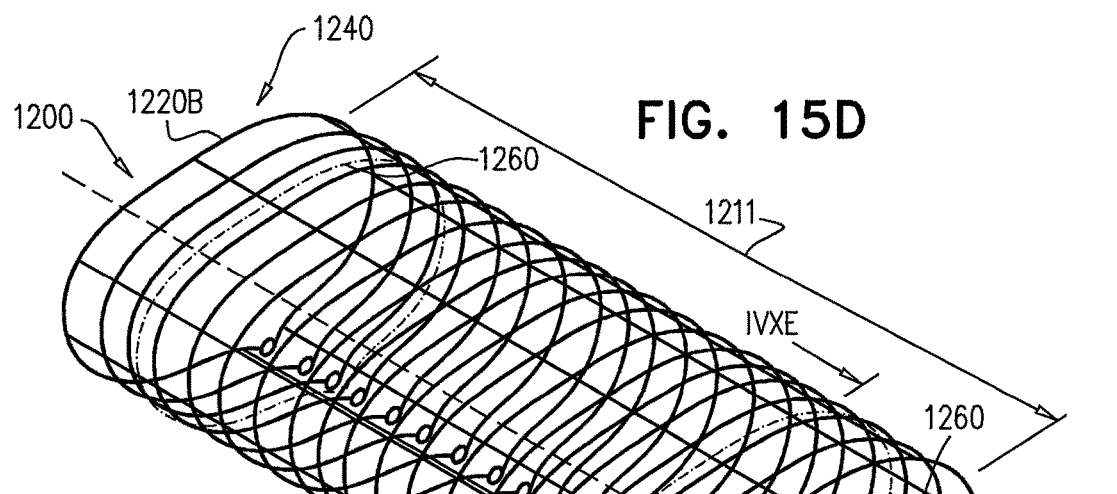
Figure 15E:
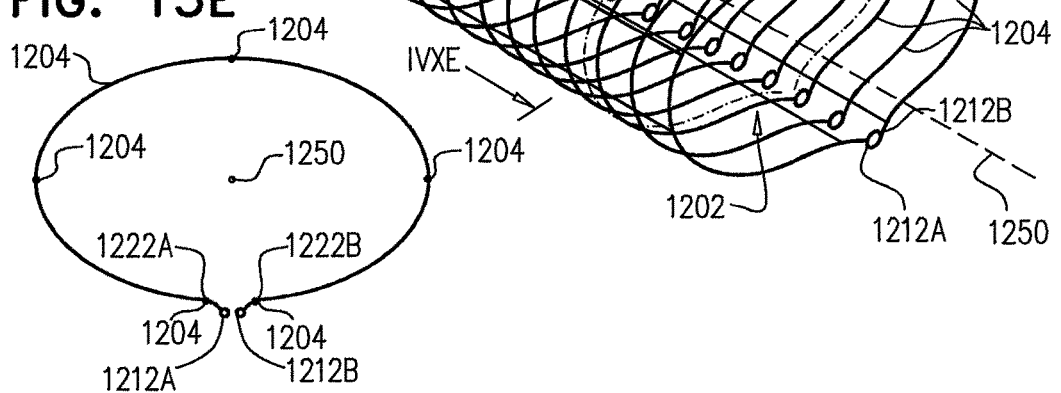

For delivery during an implantation procedure, structural member 1202 is placed in a deformed state, as shown in FIGS. 15D and 15E. (FIG. 15E is a cross-sectional view of FIG. 15D, with engagement members 1212A and 1212B, described hereinbelow, shown slightly separated for clarity of illustration.) In this state, structural member 1202 has a second elongate hollow shape 1240, different from first elongate hollow shape 1206. (For some applications, second elongate hollow shape 1240 may be different from first elongate hollow shape 1206 only in that structural member 1202 is curled in an opposite direction; first and second elongate hollow shapes 1206 and 1240 may appear to be identical. Alternatively, second elongate hollow shape 1240 may be different from first elongate hollow shape 1206 in that structural member 1202 is curled in an opposite direction, and has different dimensions with respect to the longitudinal axis. For some applications, both first and second elongate hollow shapes 1206 and 1240 are generally cylindrical, as shown in FIGS. 15A-E.) For example, second elongate hollow shape 1240 may be generally cylindrical.

For some applications, structural member 1202 assumes the deformed state by being transformed:
from first elongate hollow shape 1206 when in the relaxed state, as shown in FIG. 15A;
to planar state 1208, as shown in FIG. 15B;
to a partially curved state 1242, between planar state 1208 and the deformed state (second elongate hollow shape 1240), as shown in FIG. 15C (in FIG. 15C, proximal and distal ends 1213 and 1214 are partially brought together); and
to second elongate hollow shape 1240, as shown in FIGS. 15D and 15E.

During this transformation, structural member 1202 assumes a large number of intermediate states, which are not shown in the figures.

For some applications, when structural member 1202 has second elongate hollow shape 1240, as shown in FIGS. 15D and 15E: (i) two second sides 1222A and 1222B are generally straight and parallel with each other, and (ii) two first sides 1220A and 1220B are curved at least partially around a second longitudinal axis 1250 defined by second elongate hollow shape 1240. For some applications, two second sides 1222A and 1222B are parallel with second longitudinal axis 1250 (as shown); alternatively, the two sides are not parallel with the second longitudinal axis, such as when planar shape 1209 is a rhombus (configuration not shown). In this deformed state, two second sides 1222A and 1222B (corresponding to proximal end 1213 and distal end 1214) have been brought together. For some applications, when structural member 1202 has second elongate hollow shape 1240, two second sides 1222A and 1222B touch each other (as shown in FIG. 15D), while for other applications, the two second sides do not touch each other (such as shown in FIG. 15E).

Reference is still made to FIGS. 15A-E. For some applications, structural member 1202 is shaped so as to define a first plurality of engagement members 1212A disposed along a first one of two second sides 1222A and 1222B (e.g., second side 1222A, as shown), and a second plurality of engagement members 1212B disposed along a second one of two second sides 1222A and 1222B (e.g., second side 1222B, as shown). For example, the engagement members may comprise respective loops or small rings, as shown in the figures. First plurality of engagement members 1212A:
engage second plurality of engagement members 1212B when structural member 1202 is in the deformed state, as shown in FIGS. 15D and 15E (and FIG. 16) (such as when extra-luminal ring 1200 is removably disposed in a delivery shaft, as described hereinbelow with reference to FIGS. 17 and 18); and
do not engage second plurality of engagement members 1212B when structural member 1202 is in the relaxed state, as shown in FIG. 15A.
(First and second pluralities of engagement member 1212A and 1212B are disposed along proximal and distal ends 1213 and 1214 of structural member 1202, respectively, when structural member 1202 is in the relaxed state, as shown in FIG. 15A.)

For some applications, as shown in FIGS. 15A-E, first plurality of engagement members 1212A and/or second plurality of engagement members 1212B extend outside of planar shape 1209 (e.g., a parallelogram, such as a rectangle) generally defined by structural member 1202 when deformed to planar state 1208, as shown in FIG. 15B.

Reference is still made to FIGS. 15A-E. As mentioned above, structural member 1202 is configured, when in the relaxed state, to assume first elongate hollow shape 1206. For some applications, first elongate hollow shape 1206 geometrically defines a plurality of line segments that are straight and parallel to first longitudinal axis 1230, when the structural member is in the relaxed state, as shown in FIG. 15A. Some of these line segments are illustrated as line segments 1260 in FIGS. 15A-D (albeit not the same line segments in each of the figures). The phrase "geometrically defines," as used herein, including in the claims, is to be understood as meaning abstractly defining a geometric shape, rather than specifying a physical element of structural member 1202. In other words, no stent or other elements of structural member 1202 necessarily correspond to the line segments. When structural member 1202 is in the deformed state, as shown in FIG. 15D, the plurality of line segments geometrically defined by first elongate hollow shape 1206 are curved at least partially around second longitudinal axis 1250. (It is thus clear that a "line segment," as used herein, including in the claims, is not necessarily straight.)

Figure 16:
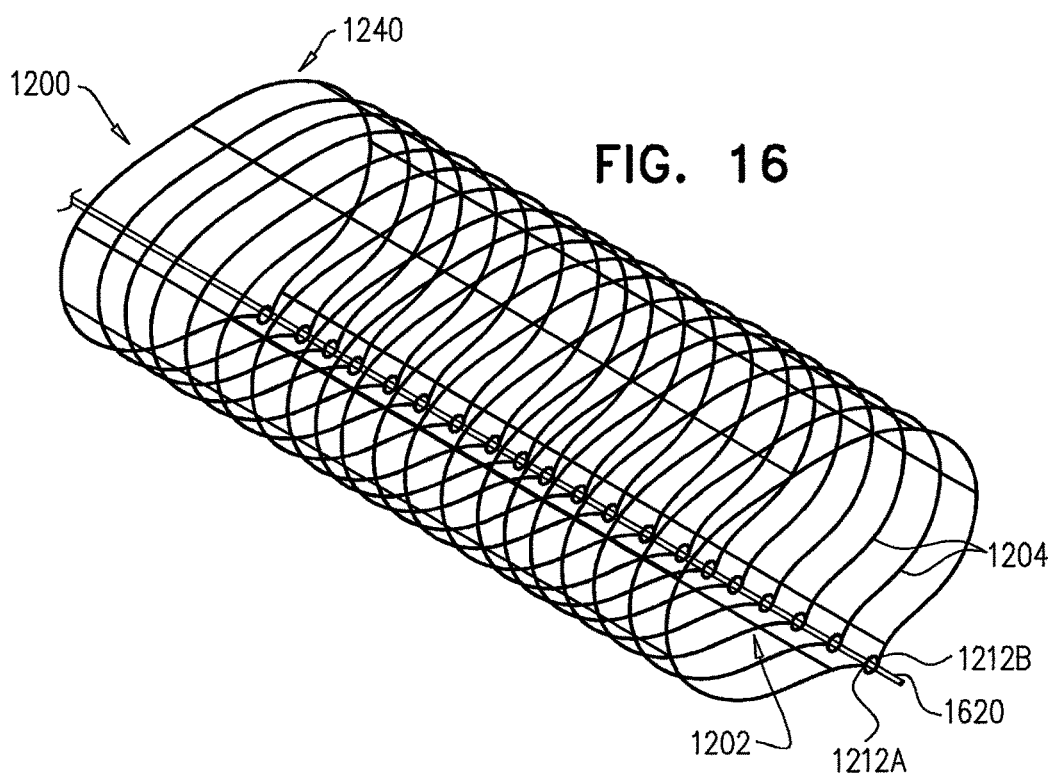
FIG. 16 is a schematic illustration of the extra-luminal ring of FIGS. 15A-E in a deformed state, in accordance with an application of the present invention.

Reference is made to FIG. 16, which is a schematic illustration of extra-luminal ring 1200 in a deformed state, in accordance with an application of the present invention. In this configuration, a longitudinal engagement element 1620, when positioned passing through first and the second pluralities of engagement members 1212A and 1212B, removably engages first plurality of engagement members 1212A with second plurality of engagement members 1212B. For some applications, longitudinal engagement element 1620 comprises a wire; alternatively, for other applications, longitudinal engagement element 1620 comprises a hollow tube. Removal of longitudinal engagement element 1620 from first and second pluralities of engagement members 1212A and 1212B (typically by sliding element 1620) allows structural member 1202 to transition to the relaxed state when otherwise no longer deformed, such as described hereinbelow with reference to FIG. 18. Alternatively, another engagement element is provided that engages and disengages the engagement members other than by sliding. For example, the engagement element may be configured to rotatably engage and disengage the engagement members (configuration not shown).

Figure 17:
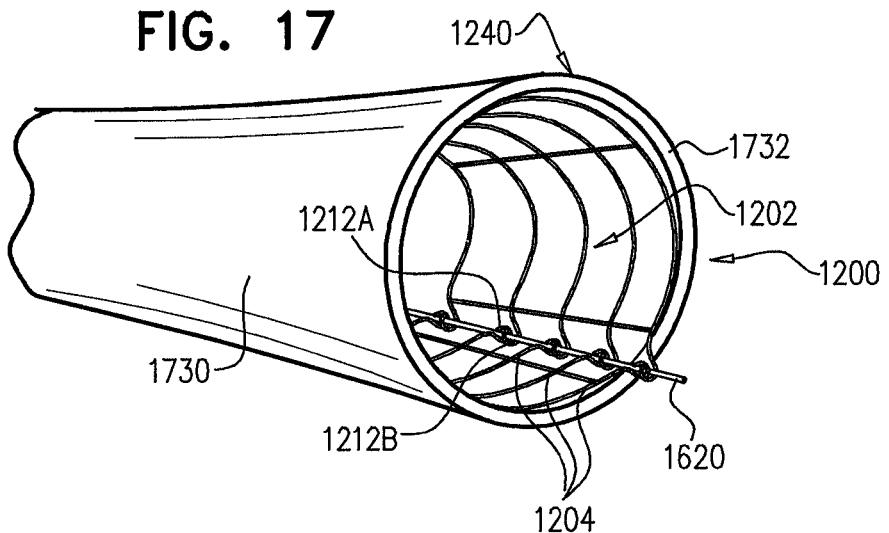
FIG. 17 is a schematic illustration of the extra-luminal ring of FIGS. 15A-E removably disposed in a delivery shaft in a deformed state, in accordance with an application of the present invention.

Reference is now made to FIG. 17, which is a schematic illustration of extra-luminal ring 1200 removably disposed in a delivery shaft 1730, in accordance with an application of the present invention. Delivery shaft 1730 is hollow and generally tubular. Structural member 1202 is in the deformed state, as also shown in FIGS. 15D and 15E. FIG. 17 also shows longitudinal engagement element 1620 engaging first plurality of engagement members 1212A with second plurality of engagement members 1212B. Alternatively, for some applications, longitudinal engagement element 1620 is not provided, in which case delivery shaft 1730 may hold structural element 1202 in the deformed state; alternatively or additionally, another mechanism holds structural element 1202 in the deformed state. Typically, extra-luminal ring 1200 is removably disposed near a distal end 1732 of delivery shaft 1730. For some applications, a portion of the delivery shaft in which extra-luminal ring 1200 is removably disposed has an inner diameter of at least 8 mm, no more than 15 mm, and/or between 8 and 15 mm.

For some applications, structural member 1202 is elongated when in the deformed state in delivery shaft 1730, such as because of geometric deformation of the structural member.

For some applications, structural member 1202 is radially compressed when in the deformed state in delivery shaft 1730. This radial compression further reduces the crossing profile of extra-luminal ring 1200, beyond the reduction because of the ratio of side lengths described hereinabove with reference to FIG. 15B. For example, for a configuration in which structural member 1202 has a diameter of about 4 cm when relaxed in first elongate hollow shape 1206, the structural member can readily be inserted into a 8 mm working channel with reasonable radial compression, representing an approximately 80% radial compression.

For some applications, structural member 1202, when in the deformed state in delivery shaft 1730, is rolled up with one or more partially overlapping layers or turns, such as at least two or three overlapping layers or turns. This rolling reduces the crossing profile of extra-luminal ring 1200. For these applications, engagement members 1212A and 1212B and longitudinal engagement element 1620 are typically not provided.

For some applications, structural member 1202 is configured to automatically transition from the deformed state to the relaxed state as the structural member is deployed from delivery shaft 1730 and longitudinal engagement element 1620, if provided, is slidingly proximally withdrawn from the engagement members. For some applications, a stopper shaft is provided within delivery shaft 1730, which prevents proximal movement of extra-luminal ring 1200 as longitudinal engagement element 1620 is proximally withdrawn.

Figure 18:
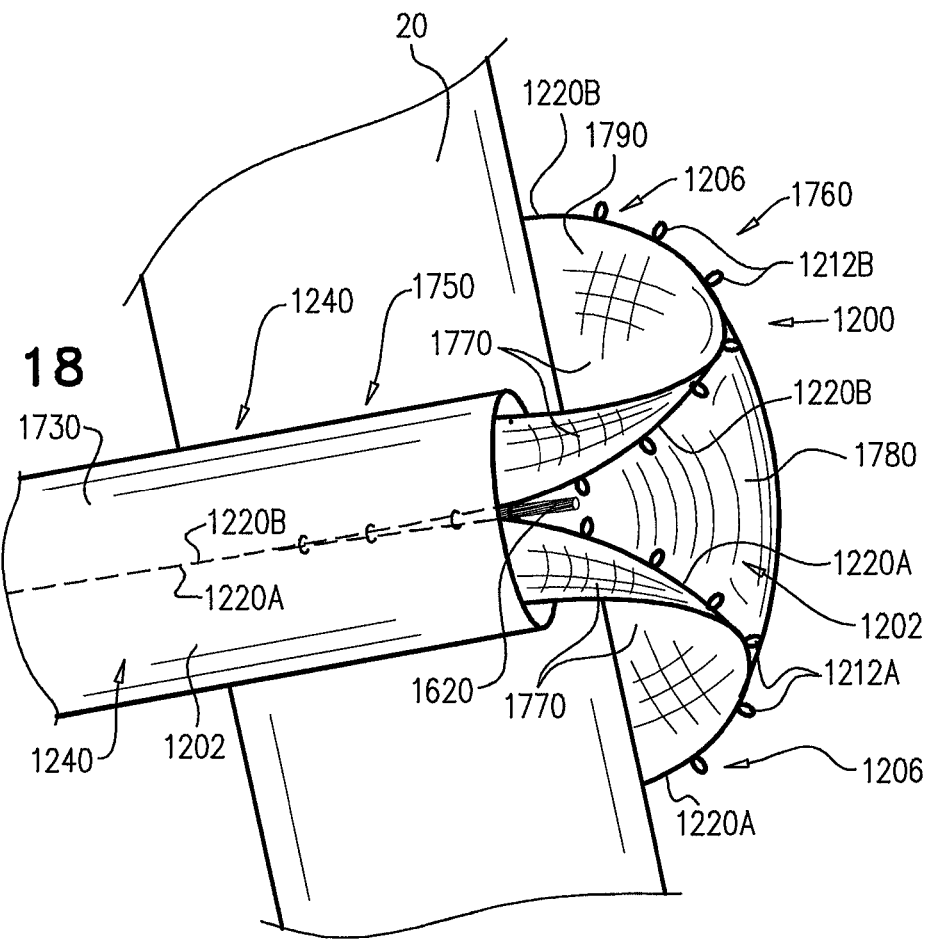
FIG. 18 is a schematic illustration of an exemplary deployment of the extra-luminal ring of FIGS. 15A-E from a delivery shaft around a tubular organ, in accordance with an application of the present invention.

Reference is now made to FIG. 18, which is a schematic illustration of an exemplary deployment of extra-luminal ring 1200 from delivery shaft 1730 around a tubular organ, e.g., aorta 20, in accordance with an application of the present invention. A surgeon creates a working channel, typically laparoscopically, to an external surface of a portion of a target organ, such as aorta 20, e.g., a neck of an aneurysmal aorta, such as a sub-renal neck immediately inferior to the renal arteries, a supra-renal neck, an ascending aortic neck, or a neck adjacent the right subclavian artery. FIG. 18 shows extra-luminal ring 1200 partially deployed from delivery shaft 1730. A first portion 1750 of extra-luminal ring 1200 remains in delivery shaft 1730 with structural element 1202 in the deformed state, and a second portion 1760 of extra-luminal ring 1200 has been deployed from delivery shaft 1730 and transitioned to the relaxed state. Longitudinal engagement element 1620 is shown proximally withdrawn from a portion of engagement members 1212A and 1212B.

Reference is still made to FIG. 18, and is additionally again made to FIG. 15B. Structural member 1202, when deformed to the planar state as shown in FIG. 15B, defines first and second (e.g., generally parallelogram-shaped, such as rectangularly-shaped) surfaces 1770 and 1780 facing away from each other. For some applications:

when structural member 1202 has first elongate hollow shape 1206 in the relaxed state, first surface 1770 faces radially inward and second surface 1780 faces radially outward; and when structural member 1202 has second elongate hollow shape 1240 in the deformed state, first surface 1770 faces radially outward and second surface 1780 faces radially inward.

(As mentioned above, FIG. 18 shows structural member 1202 partially in first elongate hollow shape 1206 in the relaxed state, and partially in second elongate hollow shape 1240.) Thus, for these applications, deploying extra-luminal ring 1200 from delivery shaft 1730 everts structural member 1202. For these applications, structural member 1202 is configured to evert itself during a transition from the deformed state to the relaxed state, during deployment from the delivery shaft. Typically, the shape memory of the structural member causes this eversion.

For some applications, extra-luminal ring 1200 further comprises an implantable-grade fabric 1790 securely attached to and at least partially covering structural member 1202 (typically on first surface 1770). The fabric is biologically-compatible, and may comprise, for example, a polyester, a polyethylene (e.g., a poly-ethylene-terephthalate), a polymeric film material (e.g., polytetrafluoroethylene), a polypropylene mesh, a polymeric textile material (e.g., woven polyethylene terephthalate (PET)), natural tissue graft (e.g., saphenous vein or collagen), or a combination thereof. For some applications, implantable-grade fabric 1790 comprises a macroporous medical textile member mention, such as described in above-mentioned US Patent Application Publication 2010/0292774 to Shalev. Alternatively or additionally, extra-luminal ring 1200 comprises an external microporous layer, such as described in the '774 publication.

As used in the present application, including in the claims, "tubular" means having the form of an elongate hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

The scope of the present invention includes embodiments described in the following applications, which are assigned to the assignee of the present application and are incorporated herein by reference. In an embodiment, techniques and apparatus described in one or more of the following patent applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

PCT Application PCT/IL2007/001312, filed Oct. 29, 2007, which published as PCT Publication WO/2008/053469 to Shalev, and U.S. application Ser. No. 12/447,684 in the national stage thereof, which published as US Patent Application Publication 2010/0070019 to Shalev U.S. Provisional Application 60/991,726, filed Dec. 2, 2007

PCT Application PCT/IL2008/001621, filed Dec. 15, 2008, which published as PCT Publication WO 2009/078010, and U.S. application Ser. No. 12/808,037 in the national stage thereof, which published as US Patent Application Publication 2010/0292774

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208, and U.S. application Ser. No. 13/380,278 in the national stage thereof, which published as US Patent Application Publication 2012/0150274

PCT Application PCT/IL2010/000549, filed Jul. 8, 2010, which published as PCT Publication WO 2011/004374

PCT Application PCT/IL2010/000564, filed Jul. 14, 2010, which published as PCT Publication WO 2011/007354, and U.S. application Ser. No. 13/384,075 in the national stage thereof, which published as US Patent Application Publication 2012/0179236

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2010/001087, filed Dec. 27, 2010, which published as PCT Publication WO 2011/080738

PCT Application PCT/IL2011/000135, filed Feb. 8, 2011, which published as PCT Publication WO 2011/095979

PCT Application PCT/IL2011/000801, filed Oct. 10, 2011, which published as PCT Publication WO 2012/049679

U.S. application Ser. No. 13/031,871, filed Feb. 22, 2011, which published as US Patent Application Publication 2011/0208289

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   an extra-luminal ring, which comprises a structural member that, if disposed in a planar state, generally defines a planar shape having two first sides parallel to each other, and two second sides parallel to each other; and
   a hollow, generally tubular delivery shaft, in which the extra-luminal ring is removably disposed for delivery with the structural member in a deformed state, in which (a) the structural member has a deformed-state elongate hollow shape, (b) the two second sides are generally straight and parallel with each other, and (c) the two first sides are curved at least partially around a deformed-state longitudinal axis defined by the deformed-state elongate hollow shape and by the delivery shaft,
   wherein the structural member is configured, upon deployment of the extra-luminal ring from the delivery shaft, to assume a relaxed state in which the structural member assumes a relaxed-state elongate hollow shape, different from the deformed-state elongate hollow shape, wherein, in the relaxed-state elongate hollow shape, (i) the two first sides are generally straight and parallel with each other, and (ii) the two second sides are curved at least partially around a relaxed-state longitudinal axis defined by the relaxed-state elongate hollow shape.

2. The apparatus according to claim 1, wherein the planar shape is a parallelogram, and wherein the structural member generally defines the parallelogram if disposed in the planar state.

3. The apparatus according to claim 2, wherein the parallelogram is a rectangle, and wherein the structural member generally defines the rectangle if disposed in the planar state.

4. The apparatus according to claim 3, wherein a ratio of (a) a length of each of the second sides to (b) a length of each of the first sides is at least 6:1.

5. The apparatus according to claim 1, wherein the relaxed-state elongate hollow shape is generally cylindrical, and wherein the structural member is configured to assume the generally cylindrical relaxed-state elongate hollow shape when in the relaxed state.

6. The apparatus according to claim 1, wherein the deformed-state elongate hollow shape is generally cylindrical, and wherein, when the extra-luminal ring is removably disposed in the delivery shaft in the deformed state, the structural member has the generally cylindrical deformed-state elongate hollow shape.

7. The apparatus according to claim 1, wherein the planar shape has rounded corners.

8. The apparatus according to claim 1, wherein the structural member, when in the relaxed state, is configured such that the two first sides are generally parallel with the relaxed-state longitudinal axis.

9. The apparatus according to claim 1, wherein the structural member, when in the deformed state, is configured such that the two second sides are generally parallel with the deformed-state longitudinal axis.

10. The apparatus according to claim 1, wherein the structural member is configured to automatically transition from the deformed state to the relaxed state as the structural member is deployed from the delivery shaft.

11. The apparatus according to claim 1,
wherein the structural member, if disposed in the planar state, defines first and second surfaces facing away from each other,
wherein when the structural member has the relaxed-state elongate hollow shape in the relaxed state, the first surface faces radially inward and the second surface faces radially outward, and
wherein when the structural member has the deformed-state elongate hollow shape in the deformed state, the first surface faces radially outward and the second surface faces radially inward.

12. The apparatus according to claim 1, wherein the structural member is configured to evert itself during a transition from the deformed state to the relaxed state, during deployment from the delivery shaft.

13. The apparatus according to claim 1, wherein the structural member is shaped so as to define a first plurality of engagement members disposed along a first one of the two second sides, and a second plurality of engagement members disposed along a second one of the two second sides, and wherein the first plurality of engagement members (a) engage the second plurality of engagement members when the extra-luminal ring is removably disposed in the delivery shaft with the structural member in the deformed state, and (b) do not engage the second plurality of engagement members when the structural member is in the relaxed state.

14. The apparatus according to claim 13, further comprising a longitudinal engagement element, which, when positioned passing through the first and the second pluralities of engagement members, engages the first plurality of engagement members with the second plurality of engagement members.

15. The apparatus according to claim 1, wherein each of the first sides has a length of between 1 and 4 cm, and each of the second sides has a length of between 6 and 15 cm.

16. The apparatus according to claim 1, wherein the extra-luminal ring is suitable for being placed at least partially around an aorta when the structural member is in the relaxed state.

17. Apparatus comprising:
an extra-luminal ring, which comprises a structural member; and
a hollow, generally tubular delivery shaft, in which the extra-luminal ring is removably disposed for delivery with the structural member in a deformed state, in which (a) the structural member has a deformed-state elongate hollow shape, which geometrically defines a plurality of line segments that are curved at least partially around a deformed-state longitudinal axis defined by the deformed-state elongate hollow shape and by the delivery shaft,
wherein the structural member is configured, upon deployment of the extra-luminal ring from the delivery shaft, to assume a relaxed state in which (a) the structural member assumes a relaxed-state elongate hollow shape, different from the deformed-state elongate hollow shape, and (b) the plurality of line segments geometrically defined by the deformed-state elongate hollow shape are straight and parallel to a relaxed-state longitudinal axis defined by the relaxed-state elongate hollow shape.

18. The apparatus according to claim 17, wherein the relaxed-state elongate hollow shape is generally cylindrical, and wherein the structural member is configured to assume the generally cylindrical relaxed-state elongate hollow shape when in the relaxed state.

19. The apparatus according to claim 17, wherein the deformed-state elongate hollow shape is generally cylindrical, and wherein, when the extra-luminal ring is removably disposed in the delivery shaft in the deformed state, the structural member has the generally cylindrical deformed-state elongate hollow shape.

20. The apparatus according to claim 17,
wherein the structural member, if disposed in a planar state, defines first and second surfaces facing away from each other,
wherein when the structural member has the relaxed-state elongate hollow shape in the relaxed state, the first surface faces radially inward and the second surface faces radially outward, and
wherein when the structural member has the deformed-state elongate hollow shape in the deformed state, the first surface faces radially outward and the second surface faces radially inward.

21. The apparatus according to claim 17, wherein the structural member is configured to evert itself during a transition from the deformed state to the relaxed state, during deployment from the delivery shaft.

22. A method comprising:
providing an extra-luminal ring, which includes a structural member that, if disposed in a planar state, generally defines a planar shape having two first sides parallel to each other, and two second sides parallel to each other;
advancing, to an external surface of a target blood vessel, a hollow, generally tubular delivery shaft, in which the extra-luminal ring is removably disposed for delivery with the structural member in a deformed state, in which (a) the structural member has a deformed-state elongate hollow shape, (b) the two second sides are generally straight and parallel with each other, and (c) the two first sides are curved at least partially around a deformed-state longitudinal axis defined by the deformed-state elongate hollow shape and by the delivery shaft; and
after advancing the delivery shaft, deploying the extra-luminal ring from the delivery shaft such that the structural member transitions from the deformed state to a relaxed state and at least partially surrounds the blood vessel, wherein in the relaxed state, the structural member assumes a relaxed-state elongate hollow shape, different from the deformed-state elongate hollow shape, wherein, in the relaxed-state elongate hollow shape, (i) the two first sides are generally straight and parallel with each other, and (ii) the two second sides are curved at least partially around a relaxed-state longitudinal axis defined by the relaxed-state elongate hollow shape.

23. The method according to claim 22, wherein the blood vessel is an aorta, and wherein deploying comprises deploying the extra-luminal ring at least partially around the aorta.

24. The method according to claim 22, wherein deploying comprises deploying the extra-luminal ring from the delivery shaft such the structural member everts itself during a transition from the deformed state to the relaxed state during deployment from the delivery shaft.

25. The method according to claim 22,
wherein the structural member, if disposed in the planar state, defines first and second surfaces facing away from each other,
wherein when the structural member has the relaxed-state elongate hollow shape in the relaxed state, the first surface faces radially inward and the second surface faces radially outward, and
wherein when the structural member has the deformed-state elongate hollow shape in the deformed state, the first surface faces radially outward and the second surface faces radially inward.

26. A method comprising:
providing an extra-luminal ring, which comprises a structural member;
advancing, to an external surface of a target blood vessel, a hollow, generally tubular delivery shaft, in which the extra-luminal ring is removably disposed for delivery with the structural member in a deformed state, in which (a) the structural member has a deformed-state elongate hollow shape, which geometrically defines a plurality of line segments that are curved at least partially around a deformed-state longitudinal axis defined by the deformed-state elongate hollow shape and by the delivery shaft; and
after advancing the delivery shaft, deploying the extra-luminal ring from the delivery shaft such that the structural member transitions from the deformed state to a relaxed state and at least partially surrounds the blood vessel, wherein in the relaxed state, the structural member assumes a relaxed-state elongate hollow shape, different from the deformed-state elongate hollow shape, wherein, in the relaxed-state elongate hollow shape, the plurality of line segments geometrically defined by the deformed-state elongate hollow shape are straight and parallel to a relaxed-state longitudinal axis defined by the relaxed-state elongate hollow shape.

* * * * *